US008691523B2

(12) United States Patent
Reid et al.

(10) Patent No.: US 8,691,523 B2
(45) Date of Patent: Apr. 8, 2014

(54) PRIMITIVE AND PROXIMAL HEPATIC STEM CELLS

(75) Inventors: Lola M. Reid, Chapel Hill, NC (US); Nicholas Moss, Carrboro, NC (US); Mark E. Furth, Chapel Hill, NC (US); John W. Ludlow, Carrboro, NC (US); Andrew T. Bruce, Holly Springs, NC (US)

(73) Assignees: Vesta Therapeautics, Inc., Bethesda, MD (US); University of North Carolina at Chapel Hill, Chapel Hill, NC (US)

( * ) Notice: Subject to any disclaimer, the term of this patent is extended or adjusted under 35 U.S.C. 154(b) by 1714 days.

(21) Appl. No.: 11/609,729

(22) Filed: Dec. 12, 2006

(65) Prior Publication Data

US 2007/0099297 A1 May 3, 2007

Related U.S. Application Data

(62) Division of application No. 10/387,547, filed on Mar. 14, 2003, now Pat. No. 7,413,897.

(60) Provisional application No. 60/365,361, filed on Mar. 15, 2002.

(51) Int. Cl.
C12N 5/00 (2006.01)

(52) U.S. Cl.
USPC ............ 435/37; 435/375; 435/325; 424/93.7

(58) Field of Classification Search
None
See application file for complete search history.

(56) References Cited

U.S. PATENT DOCUMENTS

| | | | |
|---|---|---|---|
| 5,576,207 | A | 11/1996 | Reid et al. |
| 5,665,589 | A | 9/1997 | Harris et al. |
| 5,789,246 | A | 8/1998 | Reid et al. |
| 5,843,633 | A | 12/1998 | Yin et al. |
| 6,284,451 | B1 * | 9/2001 | Funatsu et al. ............... 435/1.1 |

FOREIGN PATENT DOCUMENTS

| | | |
|---|---|---|
| JP | A 2000-287680 | 10/2000 |
| WO | WO 00/03001 A1 | 1/2000 |
| WO | WO 02/29012 A1 | 4/2002 |

OTHER PUBLICATIONS

Enat R et al. 1984. Hepatocyte proliferation in vitro: its dependence on the use of serum-free hormonally defined medium and substrata of extracellular matrix. Proc Natl Acad Sci USA 81: 1411-1415.*
Roskams, et al., "Hepatic OV-6 Expression in Human Liver Disease and Rat Experiments: Evidence for Hepatic Progenitor Cells in Man," *J. Hepatol.*, vol. 29, 1998, pp. 450-454.
De Boer, et al., "Expression of Ep-Cam in Normal, Regenerating, Metaplastic, and Neoplastic Liver," *J. Pathol.*, vol. 188, 1999, pp. 201-206.
Lemmer, et al., "Isolation from Human Fetal Liver of Cells Co-Expressing CD34 Haematopoietic Stem Cell and Cam 5.2 Pancytokeratin Markers," *J. Hepatol.*, vol. 29, 1998, pp. 455-463.
Lewin, B, ed. "Oncogenes and cancer." In: Genes VII (Oxford UK, Oxford University Press, 2000). pp. 875-876.
Lewin, B, ed. "Oncogenes and cancer." In: Genes VII (Oxford UK, Oxford University Press, 2000). pp. 875-876. QH430 .L487.
Berger et al., *Blood*, Nov. 1998, vol. 92, No. 10, Suppl. 1, part 1-2, pp. 567A.
De Boer et al., *Journal of Pathology*, Jun. 1999, vol. 188, No. 2, pp. 21-206.
Fava et al. *Journal of Clinical Oncology*, Oct. 2001, vol. 19, pp. 3951-3959.
Lemmer et al., *Journal of Hepatology*, 1998, vol. 29, pp. 450-454.
Lowes et al., "Oval cells numbers In human chronic liver diseases are directly related to disease severity," *American Journal of Pathology*, 1999, 154:537-541.
Roskams et al., *Journal of Hepatology*, 1998, vol. 29, pp. 455-463.
Smith et al., "Appearance of Oval Cells in the Liver of Rats After Long-term Exposure to Ethanol," *Hepatology*, Jan. 1996, pp. 145-154.
Wang et al., *Blood*, Nov. 2001, vol. 98, No. 11, Part 1, p. 548.
Shlomo Brill, et al., "Maturation-Dependent Changes in the Regulation of Liver-specific Gene Expression in Embryonal Versus Adult Primary Liver Cultures", Differentiation, 1995, pp. 95-102, vol. 59.
Shlomo Brill, et al., "Expansion Conditions for Early Hepatic Progenitor Cells from Embryonal and Neonatal Rat Livers", Digestive Diseases and Science, 1999, pp. 364-371, vol. 44, No. 2.
Orla M. Crosbie, et al., "In Vitro Evidence for the Presence of Hematopietic Stem Cells in the Adult Human Liver", Hepatology, Apr. 1999, pp. vol. 29, No. 4.
Aleta R. Craw Ford, et al., "The Normal Adult human Liver Biopsy: A Quantitative Reference Standard", Hepatology Aug. 1998, pp. 1193-1198, 323-331, vol. 28, No. 2.
Ira J. Fox, et al., "Treatment of the Crigler-Najjar Syndrome Type I with Hepatocyte Transplantation", The New England Journal of Medicine, May 14, 1998, pp. 1422-1426, vol. 338, No. 20.
R. Gebhardt, et al., Heterogeneous Expression of Glutamine Synthetase M RNA in Rat Liver Parenchyma Revealed by in Situ Hybridization and Northeren Blot Analysis of RNA from Periportal and Perivenous Hepatocytes•, Federation of European Biochemical Societies, Dec. 1988, pp. 89-93, vol. 241, No. 1,2.

(Continued)

Primary Examiner — Lora E Barnhart Driscoll
(74) Attorney, Agent, or Firm — Gilberto M. Villacorta; Sunit Talapatra; Foley & Lardner LLP

(57) ABSTRACT

Hepatic progenitors comprise two populations of human hepatic stem cells, primitive and proximal hepatic stem cells, and two populations of committed progenitors, one for biliary cells and one for hepatocytes. Human primitive hepatic stem cells are a very small fraction of the liver cell population and give rise to proximal hepatic stem cells constituting a much larger fraction of the liver. Human proximal hepatic stem cells give rise to biliary and hepatocyte committed progenitors. Primitive and proximal stem cells are the primary stem cells for the human liver. Human primitive hepatic stem cells may be isolated by immunoselection from human livers or culturing human liver cells under conditions which select for a human primitive hepatic stem cell. Proximal hepatic stem cells may be isolated by immunoselection, or by culturing human liver cells under conditions which include a developmental factor. Proximal hepatic stem cells may also be isolated by culturing colonies comprising a primitive hepatic stem cell under conditions which include a developmental factor. Resulting compositions may be used for treating liver disorders and for producing bioartificial organs.

12 Claims, 21 Drawing Sheets

(56) References Cited

OTHER PUBLICATIONS

J.W. Grisham, et al., " Liver Stem Cells", Stem Cells, 1997, pp. 233-282.

Samuel H. Sigal, et al., "Characterization and Enrichment of Fetal Rat Hepatoblasts by Immunoadsorption("Panning") and Flurescence-Activated Cell Sorting" Hepatology, Apr. 1994, pp. 999-1006, vol. 19, No. 4.

Samuel H. Sigal, et al., "Evidence for terminal Differentiation Process in the Rat Liver" The Journal of the International Society of Differentiation, Jul. 1995, pp. 35-42, vol. 59, No. 1.

Neil D. Theise, et al., "The Canals of Hering and Hepatic Stem Cells in Humans" Hepatology, Dec. 1999, pp. 1425-1433, vol. 30, No. 6.

Peter G. Traber, et al., "Physiologic Significance and Regulation of Hepatocellular Heterogeneity" Gastroenterology, Oct. 1988, pp. 1130-1143, vol. 95, No. 4.

Ken Zaret, et al., "Developmental Competence of the Gut Endoderm Genetic Potentiation by GATA and HNF3/Fork Head Proteins", Development Biology, May 1, 1999, pp. 1-10, vol. 209, No. 1.

Ken Zaret, et al., "Early Liver Differentiation: Genetic Potentiation and Multilevel Growth Control", Current Opinion Genetics & Development, Oct. 1998, pp. 526-531, vol. 8, No. 5.

Isabel Zvibel, et al., "Phenotypic Characterization of Rat Hepatoma Cell Lines and Lineage-Specific Regulation of Gene Expression by Differentiation Agents", Differentiation, 1998, pp. 215-223, vol. 63.

Suzuki, A. et al., "Clonal Identification and characterization of self-renewing pluripotent stem cells in the developing liver", J. Cell Biol 156: 173-184, 2002.

Schmelzer, E., et al., "Human hepatic stem cells from fetal and postnatal donors", JEM, vol. 204, No. 8, pp. 1973-1987 (Aug. 6, 20007).

Schmelzer, E., et al., "Human hepatic stem cells from fetal and postnatal donors", JEM Online Supplemental Materials, http://www.jem.org/cgi/content/full/jem.20061603/DC1, pp. 1-17 (2007).

Tateno, Chise et al., "Growth potential and differentiation capacity of adult rat hepatocytes in vitro", Wound Repair and Regeneration, 1999, vol. 7, No. 1, pp. 36-44.

\* cited by examiner

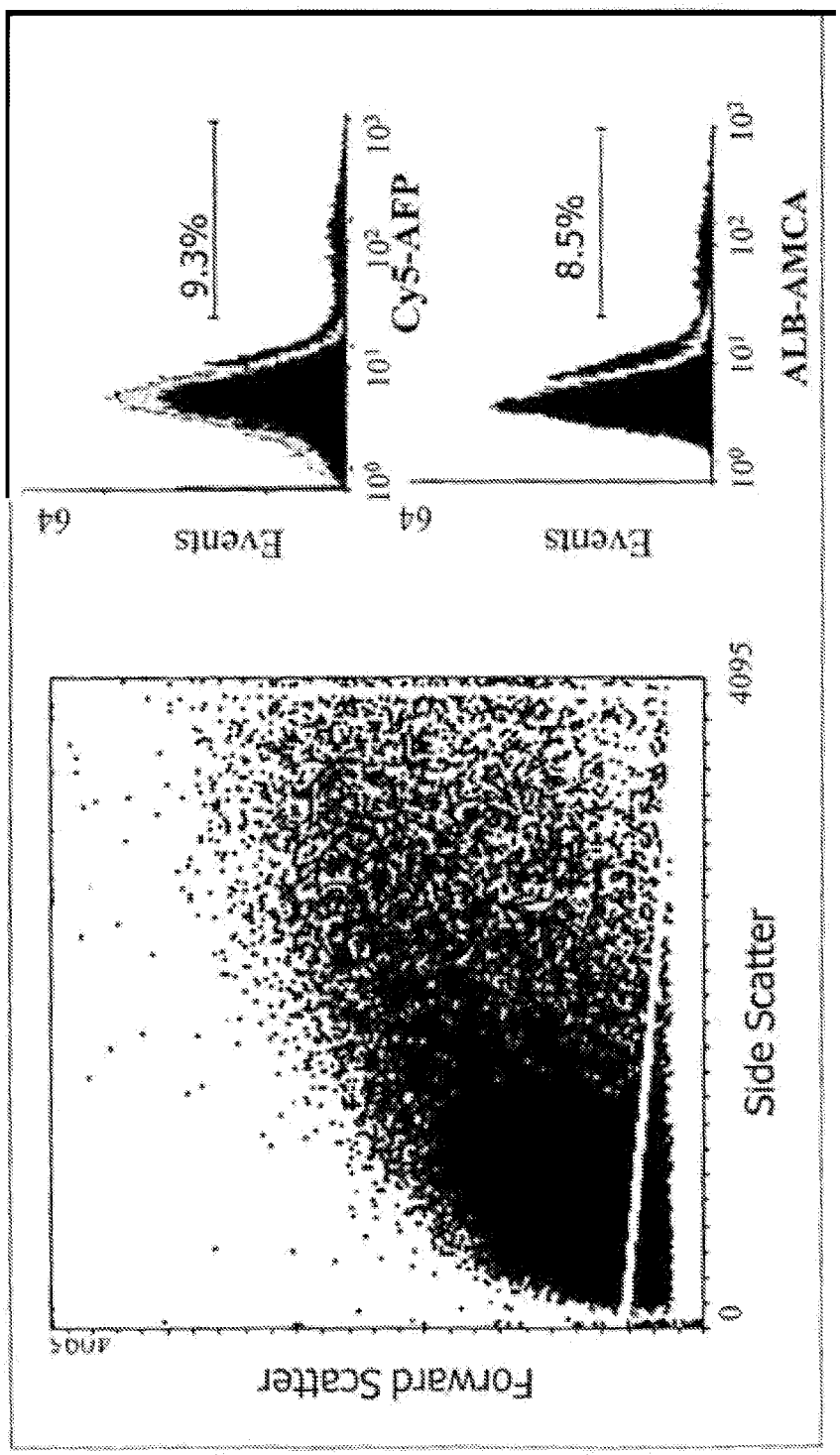
Figure 12. AFP and Albumin Expression in Original Cell Suspension

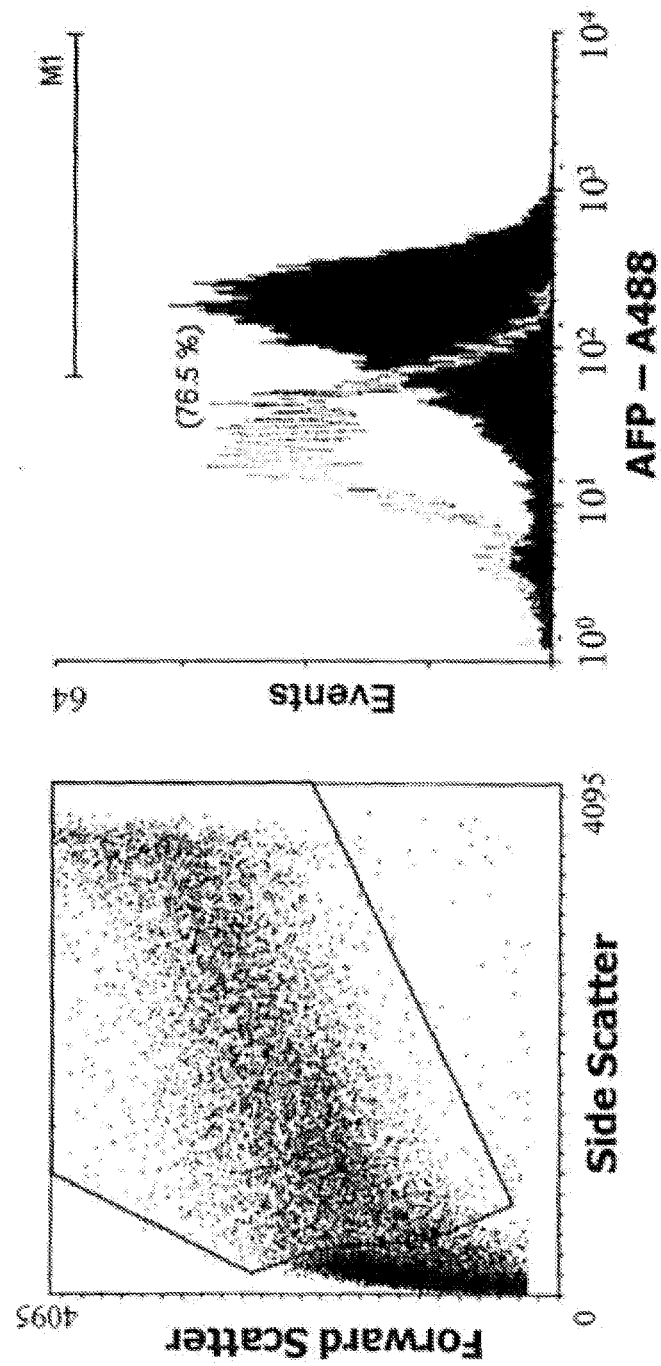
Figure 13. AFP Expression in Parenchymal Cell Preparation

Fig. 15A: expression of albumin in CD-45 depleted human liver cells
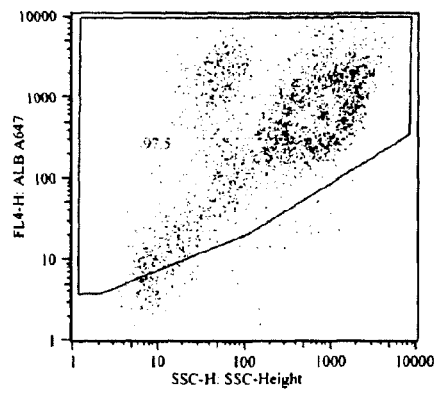
Fig. 15B: light scatter (forward and side) by albumin-positive human liver cells
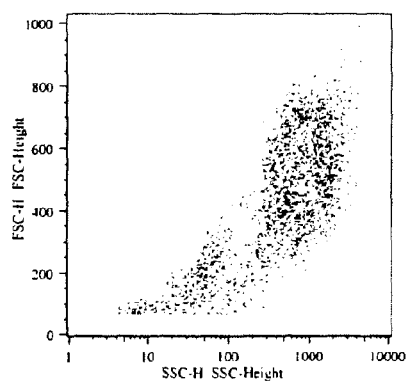
Fig. 15C: light scatter (forward and side) by albumin-negative human liver cells
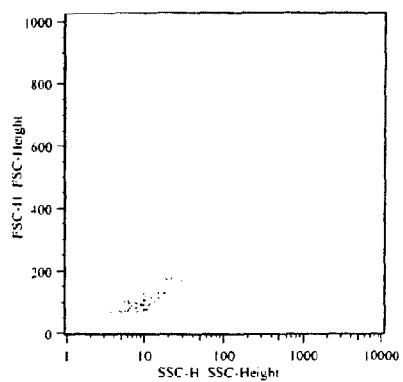

Fig. 16A: expression of CD133 protein by adult human liver cells
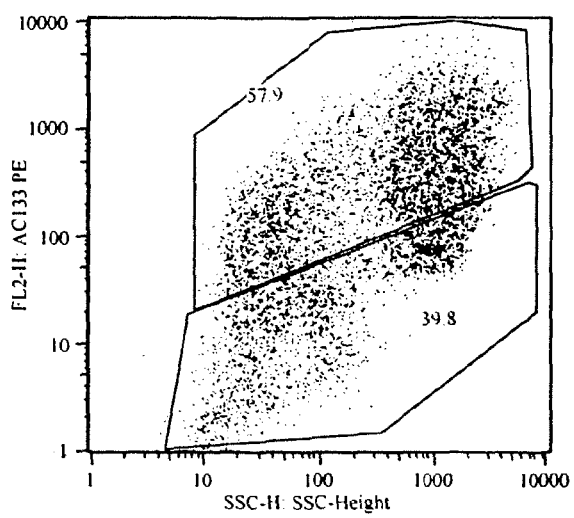
Fig. 16B enrichment of CD133-positive adult human liver cells by magnetic cell sorting
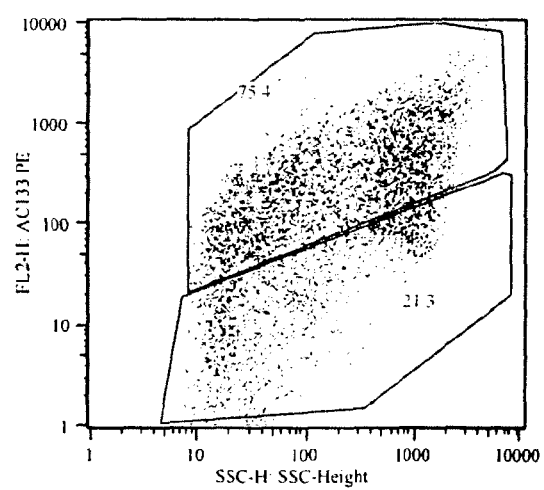

Fig. 17A & B: FACS analysis of staining of CD45-depleted human liver cells with a negative control antibody (A) and an antibody to Ep-CAM (B)
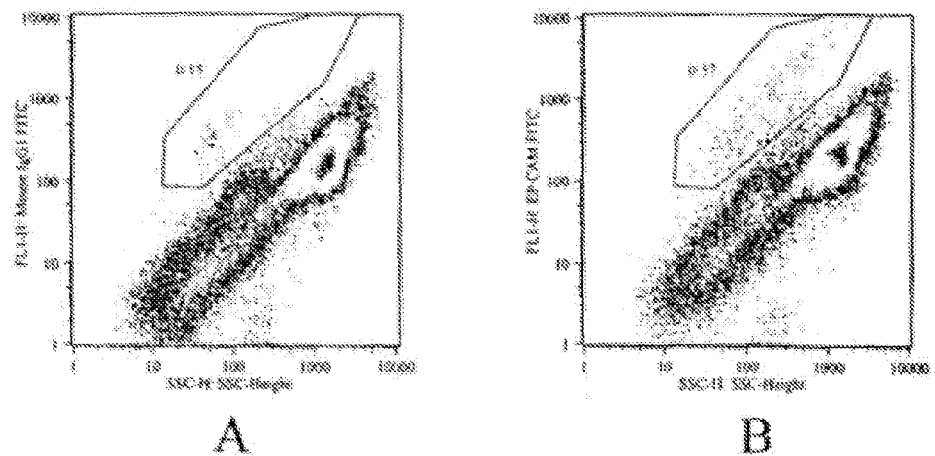
Fig. 17 C & D: FACS analysis of staining of CD45-depleted human liver cells with an antibody to CD133 (C) and co-expression of CD133 in Ep-CAM-positive cells (D)
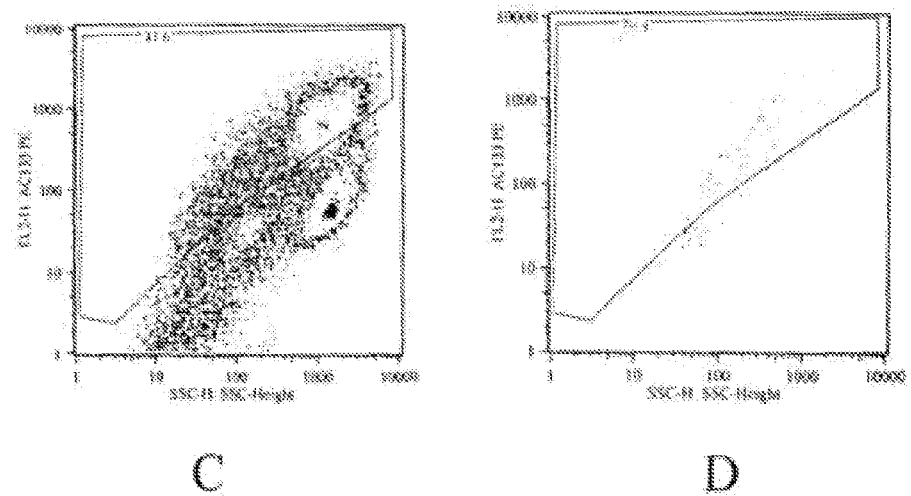

Fig. 17E: Light scatter analysis of doubly CD133-positive and Ep-CAM-positive cells.
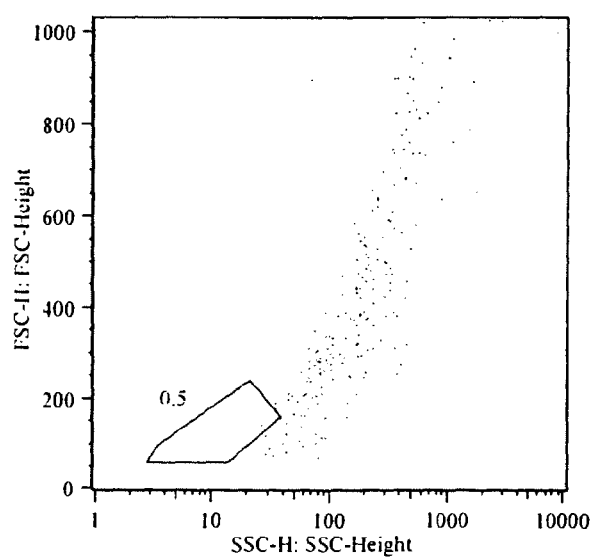
E Fig. 18: FACS analysis of staining of CD45-depleted human liver cells with a negative control antibody (A) and an antibody to Ep-CAM (B)
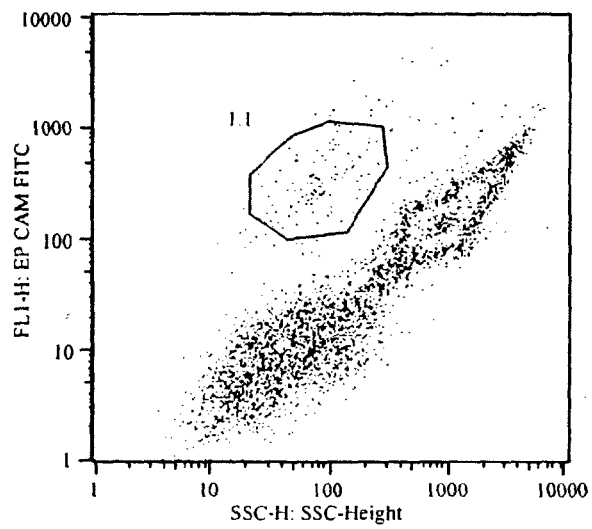
A
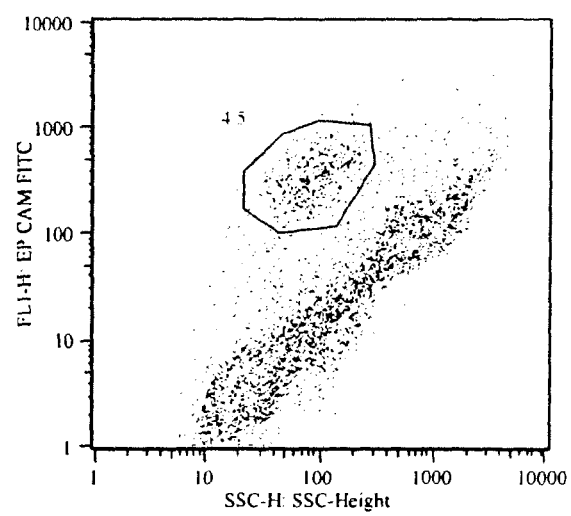
B

PRIMITIVE AND PROXIMAL HEPATIC STEM CELLS

CROSS-REFERENCE TO RELATED PATENT APPLICATIONS

This application is a Divisional of U.S. application Ser. No. 10/387,547, filed Mar. 14, 2003, now U.S. Pat. No. 7,413,897, incorporated herein by reference in its entirety, which claims priority from U.S. Provisional Application 60/365,361, filed Mar. 15, 2002, incorporated herein by reference in its entirety.

FIELD OF THE INVENTION

The present invention relates to human hepatic stem cells, pluripotent cells that give rise to mature liver cells. These include two stem cell populations: a very primitive progenitor, ductal plate stem cells, that give rise to proximal hepatic stem cells, the proximal stem cells that give rise to hepatocytes and biliary cells. The present invention also relates to methods of isolating the human hepatic ductal plate stem cells and to isolating proximal hepatic stem cells and committed hepatocytic progenitors and committed biliary progenitors. Compositions comprising cells of the present invention can be used for cell and gene therapies and for the establishment of bioartificial organs.

BACKGROUND OF THE INVENTION

1. Anatomy of the Human Liver

The primary structural and functional unit of the mature liver is the acinus, which in cross section is organized like a wheel around two distinct vascular beds: 3-7 sets of portal triads (each with a portal venule, hepatic arteriole, and a bile duct) for the periphery, and with the central vein at the hub. The liver cells are organized as cell plates lined on both sides by fenestrated endothelia, defining a series of sinusoids that are contiguous with the portal and central vasculature. Recent data have indicated that the Canals of Hering, small ducts located around each of the portal triads, produce tiny ductules that extend and splice into the liver plates throughout zone 1 forming a pattern similar to that of a bottle brush (Theise, N. 1999 Hepatology. 30:1425-1433).

A narrow space, the Space of Disse, separates the endothelia from hepatocytes all along the sinusoid. As a result of this organization, hepatocytes have two basal domains, each of which faces a sinusoid, and an apical domain which is defined by the region of contact between adjacent hepatocytes. The basal domains contact the blood, and are involved in the absorption and secretion of plasma components, while the apical domains form bile canaliculi, specialized in the secretion of bile salts, and are associated through an interconnecting network with bile ducts. Blood flows from the portal venules and hepatic arterioles through the sinusoids to the terminal hepatic venules and the central vein.

Based on this microcirculatory pattern, the acinus is divided into three zones: zone 1, the periportal region; zone 2, the midacinar region, and zone 3, the pericentral region. Proliferative potential, morphological criteria, ploidy, and most liver-specific genes are correlated with zonal location (Gebhardt, R., et al. 1988. FEBS Lett. 241:89-93; Gumucio, J. J. 1989, Vol. 19. Springer International, Madrid; Traber, P. et al. 1988. Gastroenterology. 95:1130-43). Gradients in the concentration of blood components, including oxygen, across the acinus, and following the direction of blood flow from the portal triads to the central vein, are responsible for some of this zonation, for example the reciprocal compartmentation of glycolysis and gluconeogenesis. However, the periportal zonation of the gap junction protein connexin 26 and the pericentral zonation of glutamine synthetase, to name only two, are insensitive to such gradients, are more representative of most tissue-specific genes and appear to be determined by factors intrinsic to the cells or to variables other than blood flow in the microenvironment.

In addition to hepatocytes, bile duct epithelial cells (cholangiocytes), and endothelial cells, the region between the portal and central tracts contains other cell types, such as Ito cells and Kupffer cells. These play prominent roles in pathogenic conditions of the liver, especially in inflammation and fibrosis, but their direct contribution to the main homeostatic functions of the normal organ are apparently small.

2. Development of the Human Liver

The liver develops as a result of the convergence of a diverticulum formed from the caudal foregut and the septum transversum, part of the splanchnic mesenchyme. The formation of the hepatic cells begins after the endodermal epithelium interacts with the cardiogenic mesoderm, probably via fibroblast growth factors. The specified hepatic cells then proliferate and penetrate into the mesenchyme of the septum transversum with a cord like fashion, forming the liver anlage. The direct epithelial-mesenchymal interaction is critical in these early developmental stages of the liver and dictates which cells will become hepatocytes or cholangiocytes, and the fenestrated endothelia, respectively. Mutations in the mesenchyme-specific genes hlx and jumonji block liver development, illustrating the importance of contributions from this tissue. Early in its development, the liver consists of clusters of proximal hepatic stem cells bounded by a continuous endothelium lacking a basement membrane and abundant hemopoietic cells. As the endothelium is transformed to become a discontinuous, fenestrated endothelium, the vasculature, especially the portal vasculature, becomes more developed with the production of basement membranes. The portal interstitium may provide the trigger for the development of bile ducts, and as it surrounds the portal venules, hepatic arterioles, and bile ducts, portal triads are formed. Proximal hepatic stem cells rapidly proliferate and parenchymal plates are formed, probably in response to changes in the amount and distribution of such tissue-organizing molecules as C-CAM 105, Agp110, E-cadherin, and connexins, coincident with the relocation of most, but not all, of the hemopoietic cells to the bone marrow. Recent studies suggest that some hemopoietic progenitors persist in the adult quiescent rodent liver, and hemopoietic stem cells have been isolated from both adult human and murine liver (Crosbie, O. M. et al. 1999. Hepatology. 29:1193-8).

The rat liver forms in embryonic life at about day 10, referred to as "embryonic day 10" or E10, with the invagination of the cardiac mesenchyme by endoderm located in the midgut region of the embryo (Zaret, K. 1998. Current Opinion in Genetics & Development. 8:526-31). Earliest recognition of liver cells in the embryos has been achieved by using in situ hybridization studies for mRNA encoding alpha-fetoprotein (AFP) ((Zaret, K. 1998. Current Opinion in Genetics & Development. 8:526-31; Zaret, K. 1999 Developmental Biology (Orlando). 209:1-10). AFP-expressing cells are observed in the midgut region of the embryo near the mesenchyme that produces the heart on day 9-10 in all rat and mouse livers assayed. The liver becomes macroscopically visible by E12 and is about 1 mm in diameter by E13.

In parallel, hemopoiesis occurs with the first identifiable hemopoietic cells appearing by E15-E16 (in rodents) and by the $3^{rd}$ to $4^{th}$ month (in humans) and with the peak of erythropoiesis (formation of erythroid cells or red blood cells)

occurring by E18 (in rodents) and by the $5^{th}$-$6^{th}$ month (in humans). At the peak of erythropoiesis, the numbers of these red blood cells dominate the liver and account for more than 70% of the numbers of cells in the liver. The end of the gestational period is on day 21 in rodents and 9 months in humans. Within hours of birth, the numbers of hemopoietic cells decline dramatically such that by 2 days postnatal life (rodent) and within a week or two (human), the vast majority of the hemopoietic cells have disappeared having migrated to the bone marrow. No one knows the cause for the migration of the hemopoietic cells. There are however two dominant speculations.

First, the hemopoietic progenitors prefer relatively anaerobic conditions and most of them migrate to the bone marrow (which is relatively anaerobic) with the elevated oxygen levels in the liver with the activation of the lungs. In addition, there have speculations that the loss of the pregnancy hormones may also be a factor in the migration. Postnatally, the loss of the hemopoietic progenitors in the liver is correlated with a dramatic reduction in the numbers of hepatic progenitors and a parallel increase in the numbers and maturity of the hepatocytes and biliary cells. Full maturity of the liver is completed by 2-3 weeks postnatal life (in rodents) and within a few months (humans). By then the remaining hepatic progenitor cells are localized to the regions of Canals of Hering, with the dominant numbers of them present the portal triads in the periphery of each liver acinus (Thiese et al, Crawford et al.).

Thereafter, the classic architecture of the liver acinus is established with each acinus being defined peripherally by six sets of portal triads, each one having a bile duct, an hepatic artery and an hepatic vein, and in the center a central vein that connects to the vena cava. Plates of liver cells, like spokes in a wheel, extend from the periphery to the center. By convention, the plates are divided into three zones: Zone 1 is near the portal triads; zone 2 is midacinar; and zone 3 is near the central veins. The only diploid cells of the liver are in zone 1; tetraploid cells are in zone 2; and tetraploid, octaploid and multinucleated cells are in zone 3. The pattern is highly suggestive of a maturational lineage that ends in an apoptotic process (Sigal, S. H., S. et al. 1995. Differentiation. 59:35-42).

3. Liver Disease

Each year in the United States, there are about 250,000 people hospitalized for liver failure. Liver transplants are curative for some forms of liver failure, and approximately 4100 transplants are performed a year in United States. One of the limiting factors in liver transplantation is the availability of donor livers especially given the constraint that donor livers for organ transplantation must originate from patients having undergone brain death but not heart arrest. Livers from cadaveric donors have not been successful, although recent efforts to use such donors have supported the possibility of using them if the liver is obtained within an hour of death.

Cell transplantation into the liver is an attractive alternative therapy for most liver diseases. The surgical procedures for cell transplantation are minor relative to those needed for whole organ transplantation and, therefore, can be used for patients with various surgical risks such as age or infirmity. The use of human liver cells is superior to liver cells derived from other mammals because the potential pathogens, if any, are of human origin and could be better tolerated by patients and could be easily screened before use.

Attempts to perform liver cell transplantation have made use of unfractionated mature liver cells and have shown some measure of efficacy (Fox, I. J. et al. 1998. New England Journal of Medicine. 338:1422-1426). However, the successes require injection of large numbers of cells ($2\times10^{10}$), since the cells do not grow in vivo. Furthermore, the introduction of substantial numbers of large mature liver cells (average cell diameter 30-50 µm) is complicated by their tendency to form large aggregates upon injection, resulting in potentially fatal emboli. Moreover, these cells elicit a marked immunological rejection response forcing patients to be maintained on immunosuppressive drugs for the remainder of their lives. Finally, mature liver cells have not been successfully cryopreserved and complicated logistics are required to coordinate the availability of suitable liver tissue, the preparation of cell suspensions and the immediate delivery of the cells for clinical therapies.

4. Totipotent Stem Cells

Stem cells are an alternative cell-based therapy for liver disease. Totipotent stem cells are primitive cells that can self-replicate, are pluripotent, i.e. produce daughter cells with more than one fate, that can expand extensively and that can give rise to determined stem cells that can reconstitute a tissue or tissues. Most of the literature on stem cells derives either from the literature on embryos or that on hemopoietic, epidermal, or intestinal tissues.

More recently, the definitions have been modified to recognize particular classes of stem cells. Those with the potential to participate in the development of all cell types including germ cells are referred to as totipotent stem cells and include the zygote and normal embryonic cells up to the 8 cell stage (the morula). Embryonic stem cells, also called "ES" cells, consist of permanent cell populations derived from totipotent, normal cells in blastocysts, that were first reported in the early 1980s. ES cell lines can be cultured in vitro with maintenance of totipotency. When ES cells are injected back into normal blastocysts, they are able to resume embryonic development and participate in the formation of a normal, but chimeric, mouse. Although ES cell lines have been established from many species (mouse, rat, pig, etc.), only the mouse system has been used routinely to generate animals with novel phenotypes (knockouts, transgenics) by merging modified ES cells from culture to blastocysts and then implanting the blastocysts into pseudopregnant hosts. Embryonic germ (EG) cell lines, which show many of the characteristics of ES cells, can be isolated directly in vitro from the primordial germ cell population. As with ES cells, the EG cells contributed to chimeras, including the germ line, when injected into blastocysts.

Recent, highly publicized experiments have reported that human ES cell cultures can be established from human embryos. It has been suggested that these human ES cells may be injected into tissues in the hope that they will be able to reconstitute damaged organs and tissues. However, ES and EG cells are tumorigenic if introduced into immunocompromised hosts in any site other than in utero, forming teratocarcinomas. Therefore, the plan to inoculate human ES cells into patients is unrealistic and with the grave possibility of creating tumors in the patients. To overcome this impasse, some groups are pursuing the plan of differentiating the ES cells under defined microenvironmental conditions to become determined stem cells that can then be safely inoculated into patients. For example, there is some measure of success in generating hemopoietic progenitors. However, the concern remains that residual ES cells in the culture could pose the risk of tumorigenesis, if the cultures are inoculated into a patient. In summary, until research in developmental biology reveals the myriad controls dictating the fates of cells during embryogenesis, the ES cells will remain as an experimental tool with little hope for clinical programs in cell or gene therapies. The only realistic option for clinical programs in cell and gene therapies is to use determined stem cells in which the genetic potential is restricted to a limited number of cell types.

5. Determined Stem Cells

Determined stem cells are pluripotent cells that have restricted their genetic potential to that for a limited number of cell types and have extensive growth potential. Increasing evidence such as that from the telomerase field suggest that determined stem cells do not, strictly speaking, self-replicate, that is their progeny can have less growth potential than the parent. Determined stem cells give rise to committed progenitors, daughter cells that lose pluripotency by restricting their genetic potential to a single fate, e.g. hepatocytes, whose committed progenitors are referred to as committed hepatocytic progenitors. In the hepatic lineage there are committed hepatocytic progenitors (giving rise to hepatocytes) and committed biliary progenitors (giving rise to bile ducts).

The transitions from the stem cell to the adult cells occur in a step-wise process yielding a maturational lineage in which cell size, morphology, growth potential and gene expression is tied to the lineage. The metaphor of aging is useful in defining the process. The "young" cells have early gene expression and the greatest growth potential; the cells late in the lineage have "late" gene expression and usually are limited in their growth or do not grow at all. The late cells can be considered "old" or in biological terms, apoptotic, and ultimately are sloughed off. The maturational lineage process results in a natural turnover for the tissue and allows for regeneration after injuries. Tissues differ in the kinetics of the maturational process. The maturational lineage of the gut is quite rapid with a complete cycle occurring in less than a week; that of the liver is slow occurring, and in the rat liver is about a year.

There is a strong clinical and commercial interest in isolating and identifying immature progenitor cells from liver because of the impact that such cell population may have in treating liver diseases. The use of hepatic progenitors in cell and gene therapies can overcome many of the shortcomings associated with use of mature liver cells described above. The cells are small (7-15 µm), therefore minimizing the formation of large emboli. Also, the cells have extensive growth potential meaning that fewer cells are needed for reconstitution of liver tissue in a patient. Finally, the progenitors have minimal antigenic markers that might elicit immunological rejection providing hope that little or no immunosuppressive drugs might be needed.

6. Isolation of Liver Progenitors

Isolation of liver progenitors from liver is known to be an extremely challenging task due to the shortage of markers that positively select for liver cells. The only available antibodies for candidates of hepatic progenitors are those monoclonal antibodies that are prepared against subpopulations of hepatic progenitors, called oval cells if isolated from hosts exposed to oncogenic insults. These antibodies however cross-react with antigens present in hemopoietic cells.

The term oval cells is derived from a myriad of studies in the fields of carcinogenesis and oncogenesis. Animals exposed to carcinogens or other oncogenic insults experience a dramatic loss of mature liver cells (killed by the various insults) and, secondarily, expansion of small cells (7-15 µm in diameter) with oval-shaped nuclei and bearing markers that comprised both hepatic and hemopoietic antigens (Grisham and Thorgeirrson, 1998). The studies on oval cells led to the hypotheses that they are hepatic progenitors that are triggered to expand under the conditions of the oncogenic insults and that with the proper conditions can go on to be tumor cells. The phenotype of the oval cells varies in subtle and not subtle ways depending on the oncogenic insult(s). Moreover, they are known to be readily established in culture without special feeders or medium conditions. (J. Grisham and S. Thorgeirrson, 1998, Hepatic Stem Cells, In: *Stem Cells*, C Potten, editor, Academic Press, NY). Based on these findings and on studies characterizing some of the cell lines derived from the oncogenic treatments, it was realized that liver tumors are malignantly transformed progenitors and that oval cells are partially or completely transformed progenitors (Zvibel I, Fiorino A, Brill S, and Reid L M. Phenotypic characterization of rat hepatoma cell lines and lineage-specific regulation of gene expression by differentiation agents. Differentiation 63:215-223, 1999).

Attempts have been made in the past to obtain the hepatic progenitor cell population, suggested to be the most versatile population for cell and gene therapy of the liver. U.S. Pat. Nos. 5,576,207 and 5,789,246 (Reid et al.) utilize cell surface markers and side scatter flow cytometry to provide a defined subpopulation in the liver. Subpopulations of rat hepatic cells have been isolated by removal of lineage-committed cells followed by selection for immature hepatic precursors which were detected as being agranular cells bearing OC.3-positive (oval cell antigenic marker), AFP-positive, albumin-positive, and CK19-negative (cytokeratin 19) cell markers. The foregoing rat liver subpopulations demonstrate particular characteristics important in isolation and identification of enriched hepatic progenitors from rodent liver.

Thus, there exists a need to develop methods of isolating human hepatic progenitors that may be used to treat patients with liver disease or dysfunction. The present invention satisfies this need and provides methods of treatment as well.

SUMMARY OF THE INVENTION

The present invention is directed to a composition comprising a human primitive hepatic stem cell that is a precursor to a proximal hepatic stem cell, hepatocytic progenitor, or biliary progenitor. The human primitive hepatic stem cell of the invention expresses ep-CAM, AC133, and albumin.

Another embodiment of the present invention is a composition comprising a human proximal hepatic stem cell that is a precursor to a hepatocytic or biliary progenitor. The human proximal hepatic stem cell of the invention expresses alpha-fetoprotein, albumin, and cytokeratin 19.

Another embodiment of the present invention is a method for isolating a human hepatic progenitor comprising identifying a cell that expresses ep-CAM and AC133. The human hepatic progenitor isolated by the present method preferably expresses albumin. In a preferred embodiment of the present invention, the isolated human hepatic progenitor is a stem cell, preferably a primitive hepatic stem cell or a proximal hepatic stem cell.

Another embodiment of the present invention is a method for isolating a human primitive hepatic stem cell comprising culturing a mixture of cells derived from human liver tissue on a surface under conditions which select for a hepatic stem cell with serum-free media comprising a regulator of carbohydrate metabolism, an iron carrier, and a membrane producing factor, whereby a colony is formed comprising a human primitive hepatic stem cell. In a preferred embodiment of the present invention, the isolated human primitive hepatic stem cell expresses ep-CAM, AC133, and albumin, and preferably further expresses cytokeratin 8/18 and cytokeratin 19.

Another embodiment of the present invention is a method for isolating a human proximal hepatic stem cell comprising culturing a mixture of cells derived from human liver tissue on a surface under conditions which select for a hepatic stem cell with serum-free media comprising a regulator of carbohydrate metabolism, an iron carrier, and a membrane producing factor, whereby a colony is formed comprising a human primitive hepatic stem cell, and culturing the cells from the colony with a developmental factor. In a preferred embodiment of the present invention, the isolated human proximal hepatic stem cell expresses alpha-fetoprotein, albumin, and cytokeratin 19. In a preferred embodiment of the present invention, the developmental factor is provided by a secondary cell, preferably a feeder cell, preferably an STO feeder cell, an endothelial cell, or a stromal cell.

Another embodiment of the present invention is a method for isolating a human proximal hepatic stem cell comprising culturing a mixture of cells derived from human liver tissue under conditions which select for a hepatic stem cell with serum-free media comprising a regulator of carbohydrate metabolism, an iron carrier, and a membrane producing factor, whereby a colony is formed comprising a human primitive hepatic stem cell, and culturing the cells from the colony with a developmental factor. In a preferred embodiment of the present invention, the isolated human proximal hepatic stem cell expresses alpha-fetoprotein, albumin, and cytokeratin 19. In a preferred embodiment of the present invention, the developmental factor is provided by a secondary cell, preferably a feeder cell, preferably an STO feeder cell, an endothelial cell, or a stromal cell.

Another embodiment of the present invention is an isolated primitive hepatic stem cell. Yet another embodiment of the present invention is an isolated human proximal hepatic stem cell.

BRIEF DESCRIPTION OF THE DRAWINGS

FIGS. 12 and 13 demonstrate the enrichment of AFP-expressing cells in human liver cells.

FIGS. 14-18 demonstrate the isolation of a subpopulation of adult human liver cells co-expressing albumin, CD133, and Ep-CAM.

Figure 1:
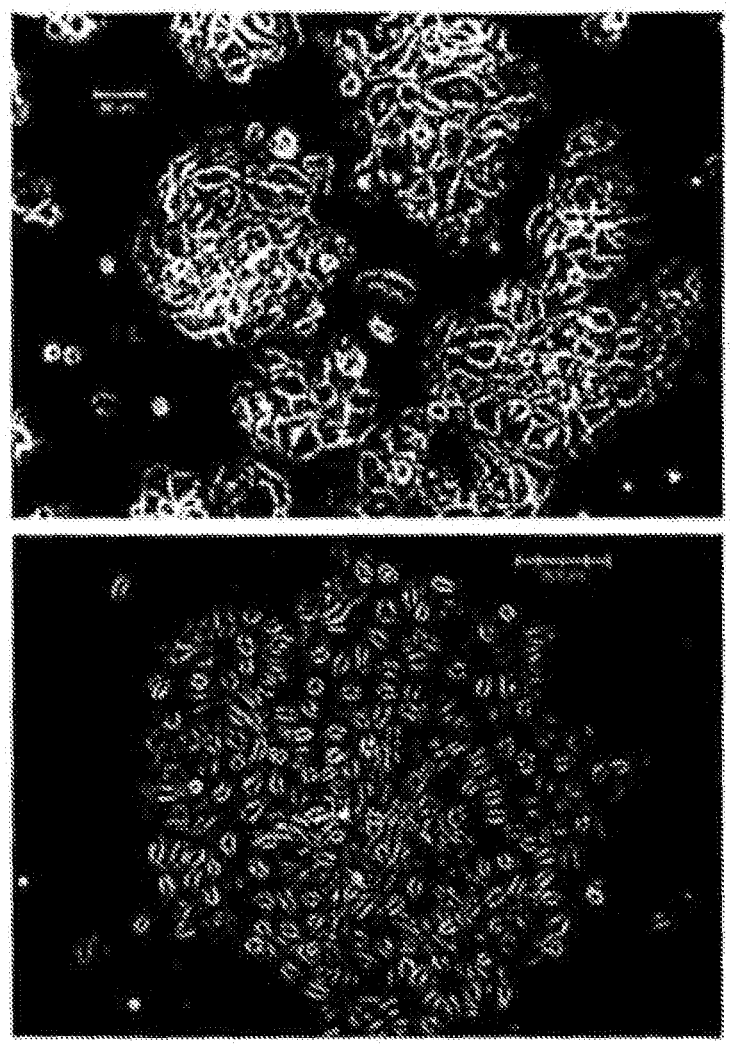
FIG. 1 demonstrates colony formation on plastic culture from enriched fetal parenchymal cells on plastic culture Day 1 (Top Panel) and Day 5 (Bottom Panel).

In the left hand grouping two cell fractions are shown (P and I) based upon centrifugation through Ficoll. Cells which pelleted in the Ficoll are designated P, and cells that become layered at the interface between aqueous medium and Ficoll are designated I. The single middle blot shows the albumin and AFP expression in purified colony cells (primitive hepatic stem cells) cultured on plastic for 3 weeks. The right hand panel shows control lanes in which there was either no protein (blank), albumin (ALB) or alpha fetoprotein (AFP) standards. 10 ug of protein was loaded in each lane.

DETAILED DESCRIPTION OF THE INVENTION

1. Definitions

In the description that follows, a number of terms are used extensively to describe the invention. In order to provide a clear and consistent understanding of the specification and claims, including the scope to be given such terms, the following definitions are provided.

CD: "Cluster of differentiation" or "common determinant" as used herein refers to cell surface molecules recognized by monoclonal antibodies. Expression of some CDs are specific for cells of a particular lineage or maturational pathway, and the expression of others varies according to the state of activation, position, or differentiation of the same cells.

Cell Therapy: As used herein, the term "cell therapy" refers to the in vivo or ex vivo transfer of defined cell populations used as an autologous or allogenic material and transplanted to, or in the vicinity of, a specific target cells of a patient. Cells may be transplanted in any suitable media, carrier or diluents, or any type of drug delivery systems including, microcarriers, beads, microsomes, microspheres, vesicles and so on. They can also be used in a bioreactor in which they provide critical functions and the bioreactor used as an assist device for patients with liver dysfunction(s).

Committed Progenitors: Highly proliferative cells that that gives rise to daughter cells of only one fate. A "biliary committed progenitor" gives rise to bile ducts and can be recognized antigenically by the expression of cytokeratin 19, but not AFB. A "hepatocytic committed progenitor" gives rise to hepatocytes and can be recognized antigenically by the expression AFP and albumin, but not cytokeratin 19. The commitment process is not understood on a molecular level. Rather, it is recognized to have occurred only empirically when the fates of cells have narrowed from that of a predecessor.

Gene Therapy: As used herein, the term "gene therapy" refers to the in vivo or ex vivo transfer of defined genetic material to specific target cells of a patient, thereby altering the genotype and, in most situations, altering the phenotype of those target cells for the ultimate purpose of preventing or altering a particular disease state. This can include modifying the target cell ex vivo and introducing the cells into the patient. Alternatively, a vector can be targeted to liver progenitor cells in vivo to deliver the exogenous genetic material and transfect the progenitors. Furthermore, genetically engineered progenitor cells can be used in a bioreactor as a therapy for patients or as source of biological products. As this definition states, the underlying premise is that these therapeutic genetic procedures are designed to ultimately prevent, treat, or alter an overt or covert pathological condition. In most situations, the ultimate therapeutic goal of gene therapy procedures is to alter the phenotype of specific target cell population.

Hepatic Cells: A subpopulation of liver cells which includes hepatocytes and biliary cells.

Hepatic Progenitors: A subpopulation of stem cells, these cells ultimately give rise to mature parenchymal cells that comprise hepatocytes and biliary cells. The hepatic progenitors include the following two subpopulations: (a) hepatic stem cells and (b) committed progenitors.

Hepatic Stem Cells: A subpopulation of hepatic progenitors, including "primitive hepatic stem cells" and "proximal hepatic stem cells".

Precursor: As used herein, the term "precursor" refers to a first type of cell that gives rise to a second type of cell. The precursor may directly give rise to the second type of cell. The precursor may also give rise to the second type of cell, through one or more other intermediary cell types.

Primitive Hepatic Stem Cells: As used herein, the term "primitive hepatic stem cells" refers to hepatic stem cells that give rise to proximal hepatic stem cells.

Proximal Hepatic Stem Cells: As used herein, the term "proximal hepatic stem cells" refers to hepatic stem cells that give rise to hepatocytes and biliary epithelial cells.

Liver Cells: As used herein, the term "liver cells" refers to all type of cells present in normal liver, regardless of their origin or fate.

Stem Cells: As used herein, the term "stem cells" refers to highly proliferative cells that can give rise to daughter cells with more than one fate, that is they are pluripotent. Totipotent stem cells, such as embryonic stem cells (ES cells) or embryonic cells up to the 8 cell stage of a mammalian embryo, have self-renewal (self-maintaining) capacity in which the stem cell produces a daughter cell identical to itself. By contrast, determined stem cells, such as hemopoietic, neuronal, skin or hepatic stem cells, are pluripotent and have extensive growth capacity but have questionable self-renewal capacity. In the case of totipotent stem cells, some daughter cells are identical to the parent, and some "commit" to specific fate(s) restricting their genetic potential to that which is less than the parent's. In the case of determined stem cells, some daughter cells retain pluripotency and some lose it, committing to a single, specific fate.

When the terms "one," "a," or "an" are used in this disclosure, they mean "at least one" or "one or more," unless otherwise indicated.

2. Diagnostic Markers for Hepatic Lineages.

Alpha-fetoprotein (AFP) and albumin, both cytoplasmic proteins, are especially reliable markers for hepatic lineages when assayed as proteins. Messenger RNAs encoding variant forms of these proteins are expressed in hemopoietic progenitors but are not translated; for example, a variant form of AFP mRNA differing from that in hepatic cells by replacement of the exon 1 encoded sequences with either an alternate exon 1 or two exons (Kubota, Storm and Reid, submitted; also in patent application). Therefore, the expression of these two proteins is the foundation for identification of the hepatic subpopulations from other cell types in the liver. Within the developing liver the presence of AFP and albumin is recognized as a strong positive indicator of hepatic progenitor cells. In the earliest stages of liver development these cells are capable of producing offspring that enter both biliary and hepatocyte lineages. If these daughter cells commit to the biliary lineage AFP expression ceases. However, AFP expression persists in the hepatocyte lineage until the perinatal period when it is suppressed, leaving albumin expression as one of the principal characteristics of the adult hepatocyte.

3. Processing of Human Liver Progenitors

The isolation of liver cells usually involves enzymatic and mechanical dissociation of the tissue into single cell suspensions followed by fractionation with density gradient centrifugation, centrifugal elutriation, differential enzymatic digestion protocols (i.e., hepatic stellate cells), and/or with selection using cell culture (reviewed in Freshney, "Culture of Animal Cells, A Manual of Basic Technique" 1983, Alan R Liss, Inc. NY). Liver tissue may be obtained from a fetus, a neonate, an infant (birth to 1 year old), a child (1 year old to puberty), or an adult (beyond puberty). Density gradient centrifugation is preferably used to fractionate and isolate different cell populations (e.g., hepatoblasts).

4. Culturing of Proximal Hepatic Stem Cells and Other Progenitors

Proximal hepatic stem cells and committed hepatic progenitors require embryonic liver stromal feeders and a serum-free medium supplemented with a mixture of defined hormones and growth factors [1-6]. Clonogenic expansion and prolonged maintenance of key markers of the proximal hepatic stem cells, of committed progenitors and of diploid adult liver cells can occur if the embryonic liver stromal feeders are substituted with STO feeder cells in combination with a serum-free, hormonally defined medium supplemented with insulin, transferrin/Fe and preferably hydrocortisone [7]. Given that these conditions support a diverse range of progenitors from fetal tissue and even colony formation of diploid adult cells [7], different conditions are needed to select for the primitive hepatic stem cells 5. Isolation of Primitive Hepatic Stem Cells The present invention involves a method of isolating primitive hepatic stem cells from human liver tissue comprising applying a cell suspension derived from liver tissue, preferably enriched for parenchymal cells, to a plastic surface and subjecting the cells to stringent culture conditions that eliminate mature liver cells, the proximal hepatic stem cells and the committed progenitors. Stringent culture conditions include the use of serum-free medium supplemented with a regulator of carbohydrate metabolism, a source of iron, a membrane producing factor, and preferably an anti-oxidant.

A preferred regulator of carbohydrate metabolism is insulin. A preferred source of iron is transferrin. A preferred membrane producing factor is a composition comprising one or more lipids, most preferably, free fatty acid. A preferred anti-oxidant is selenium. The serum-free medium is preferably further supplemented with hydrocortisone. The liver tissue is preferably obtained from a fetus, a neonate, an infant, a child, a juvenile, or an adult, and most preferably, from a fetus.

Primitive hepatic stem cells are isolated by culturing the liver-derived cell suspension on a plastic surface at low cell densities (e.g. 1000-2000 cells/cm$^2$). The stringent culture conditions result in emergence of primitive hepatic stem cells from human liver which are precursors to proximal hepatic stem cells. These primitive hepatic stem cells from human liver co-express Ep-CAM, AC133, CK8/18, CK19, and albumin and subpopulations of them express N-CAM, CAM 5.2, and c-kit.

One of skill in the art will recognize that the present invention may be used to isolate primitive cells from other tissue types.

6. Isolation of the Proximal Hepatic Stem Cells

Human proximal hepatic stem cells give rise to hepatocytes or biliary epithelia, or combinations thereof. Human proximal hepatic stem cells co-express Ep-CAM, CK8/18, cytokeratin 19, alpha-fetoprotein, and albumin and subpopulations express AC133. Human proximal hepatic stem cells can be isolated by various methods, including (i) immunoselection of cells that co-express EP-CAM (ii) culturing liver derived cell suspensions, preferably enriched for parenchymal cells, with a developmental inducing factor, or (iii) culturing human primitive hepatic stem cells with a developmental inducing factor. The developmental inducing factor is preferably provided by a secondary cell. Preferred secondary cells include an STO feeder cell, an embryonic liver stromal cell, or an endothelial cell.

7. Isolation of Hepatic Progenitor by Immunoselection

The present invention also involves a method of isolating a hepatic progenitor from liver-derived cell suspensions based on immunoselecting cell surface markers specific for a hepatic progenitor. A hepatic progenitor may be isolated according to the present invention by selecting for cells that express ep-CAM, and preferably those cells that further express AC133. The immunoselected hepatic progenitor of the present invention preferably further express albumin, and more preferably further express cytokeratin 19. Preferably, the immunoselected hepatic progenitor is a stem cell.

In one embodiment of the present invention, the isolated hepatic progenitor is a primitive hepatic stem cell. In another embodiment of the present invention, the isolated hepatic progenitor is a proximal hepatic stem cell.

8. Production of Hepatic Progenitors

The present invention also involves a method of producing proximal hepatic stem cells and committed progenitors from hepatic primitive hepatic stem cells comprising either directly plating onto STO feeder layers and in the HDM or by transferring the primitive hepatic stem cells from colonies on culture plastic to a STO feeder layer and allowing the proximal hepatic stem cells to emerge from the colonies of primitive hepatic stem cells.

Proximal hepatic stem cells and committed progenitors may also be produced from primitive hepatic stem cells by culturing on uncoated surfaces, including petri dishes (preferably non-charged polystyrene surfaces), tissue culture plastic (preferably polystyrene surfaces exposed to ionizing gas so that the polystyrene is polarized with a preferential orientation of negative (or positive) charges towards the side to which the cells are to attach), microcarriers (preferably culture beads to which cells can be bound), textile fabrics (preferably nylon, cotton, polyester), synthetic scaffoldings (preferably made from polylactides, poly(propylene fumarate), poly(ortho esters), or other synthetic materials) or sponges (preferably natural or synthetic sponges).

Proximal hepatic stem cells and committed progenitors may also be produced from primitive hepatic stem cells by culturing on biological surfaces. The biological surfaces can be coated or prepared onto the surfaces in the categories above. Thus, for example, one can coat extracellular matrix coatings onto petri dishes, tissue culture plastic, microcarriers or textile fabrics. Biological surfaces used in the present invention include (i) extracellular matrix (a complex mixture of proteins and carbohydrates produced by cells and located outside and between cells and comprising collagens, adhesion proteins, proteoglycans, and other proteins), (ii) extracellular matrix components (individual, purified matrix components used alone or in combinations for optimization of cell attachment, growth and/or expression of tissue-specific function(s), including fibronectin, laminin, collagens (there are more than 20 families of collagens) including type I collagen, type III collagen, type IV collagen (these three are the most commonly used today in cell culture), cell adhesion molecules or "CAMs" some of which are calcium-dependent and some of which are not, and proteoglycans (molecules that consist of a core protein to which is attached one or more glycosaminoglycan chains, polymers of a dimeric unit of glucuronic acid or iduronic acid+an aminosugar). These include chondroitin sulfate proteoglycan, dermatan sulfate proteoglycan, heparan sulfate proteoglycan, heparin proteoglycan), (iii) tissue extracts enriched in extracellular matrix, including Matrigel (a urea extract of a transplantable murine embryonal carcinoma. Can be coated onto any of the surfaces given in group I)), ECM (extraction of cultured cells using dilute alkali, dilute detergent, high salt extraction, urea, etc. and leaving behind an exudate enriched in extracellular matrix components coating the surface (any of those in group I)), amniotic membrane matrix (extraction of amnions with dilute alkali, dilute detergent, high salt extraction, urea, etc. and leaving behind matrix components present in the amnions), and biomatrix (extraction of tissue with high salt (e.g. >3 M NaCl) and nucleases to leave behind all the tissue's collagens and any associated components such as adhesion proteins), (iv) serum coating (if one coats petri dishes or tissue culture dishes with serum, one adds adhesion proteins, especially fibronectin, present in high levels in serum), and (v) polylysine or polyleucine (coating with these positively charged amino acids is used to attach epithelial cells preferentially).

Proximal hepatic stem cells and committed progenitors may also be produced from primitive hepatic stem cells by culturing under condition described in Anthony Atala and Robert P. Lanza, editors. Methods of Tissue Engineering. Academic Press, New York 2002, which is incorporated herein by reference. Hepatic progenitors produced by the present invention include primitive and proximal hepatic stem cells, hepatocytic committed progenitors, and biliary committed progenitors.

9. Therapeutic Approaches

The isolated progenitors of the present invention may be used for liver-directed cell and/or gene therapy or as cells to be hosts for virus production (e.g. hepatitis C) to generate vaccines. Also, the progenitors of the present invention may be expanded ex vivo from liver biopsies (e.g. punch biopsy) and the expanded cells used for autologous or allogeneic cell or gene therapies or used to seed bioreactors to create bioartificial livers that can be used clinically or for academic studies. This would eliminate the necessity for major invasive surgical resection of the patient's liver.

Once the progenitors are established in culture, gene transfer may be performed using any of a number of different gene delivery vector systems. The growing characteristics of the progenitors of this invention permits the use in an ex vivo gene transfer using certain gene delivery vectors (i.e., retroviral vectors) which will require cell proliferation for efficient gene insertion and expression.

An alternative approach for gene therapy is to design vectors that target the progenitors specifically and then to inject the vector, coupled with the gene of interest, directly into the patient. The vectors would target and modify the endogenous progenitor cell population.

The progenitor of this invention can be used in an autologous or allogeneic liver-directed cell or gene therapy. Clearly, the use of autologous hepatic progenitors will eliminate a significant concern regarding rejection of the transplanted cells. The progenitors of this invention are particularly attractive for allogenic cell transfer, because their antigenic profile suggests minimal immunological rejection phenomena.

Once the autologous or allogenic progenitors are isolated purified and cultured, they can be genetically modified or remain intact, expanded in vitro, and then transplanted back into the host. If genetic modification is desired, after genetic modification and before transplant, those genetically modified cells may be expanded and/or selected based on the incorporation and expression of a dominate selectable marker. Transplant can be back into the hepatic compartment or an ectopic or heterotopic site. For transplant into the hepatic compartment, portal vein infusion or intrasplenic injection could be used. Intrasplenic injection may be the administration route of choice because hepatic progenitors transplanted via an intrasplenic injection move into the hepatic compartment.

Additional medical procedures may assist in the efficacy of hepatic engraftment of the transplanted hepatic progenitors. Animal models have demonstrated that in partial hepatectomy, administration of angiogenesis factors, and other growth factors aide in the engraftment and viability of the transplanted hepatocytes. An alternative approach is to transplant the genetically modified progenitors to an ectopic site.

To date, there have been problems associated with hepatic cell therapy approaches including sourcing of the cells, inability to cryopreserve cells, emboli formation, and immunological rejection, etc.) The problems with current hepatic cell therapy approaches may be due to the fact that the donor cells being used are predominantly adult liver cells and are short-lived after isolation and reinjection. In addition, the use of adult cells results in strong immunological rejection. The progenitors cells of the instant invention offer greater efficacy because of their limited capacity to elicit immunological rejection phenomena, their ability to be cryopreserved and therefore offering opportunities to tissue type them (and thereby match the donor cells to the recipient) and to offer an "off-the shelf" product, and because of their extensive regenerative potential.

With respect to gene therapy, the ongoing efforts make use of "targeted injectable vectors," the most popular route for clinical therapies under development. These approaches have had limited efficacy due both to immunological problems and transient expression of the vectors. The only routes for gene therapy that have proven merit-worthy have been ex vivo gene therapy and have been done almost exclusively in hemopoietic progenitor cells. We predict that ex vivo gene therapy with progenitors cells (or use of injectable vectors somehow targeted to those progenitors) will prove more effective, since the vectors can be introduced ex vivo into purified progenitor cells; the modified cells selected and reintroduced in vivo. The advantages of the progenitor cells are their enormous expansion potential, their minimal, if any, induction of immunological reactions or ability to be tissue typed and therefore matched to the recipient's immunological phenotype, and their ability to differentiate to produce both hepatocytes and biliary cells.

10. Other Uses

The uses for human hepatic primitive and proximal hepatic stem cells are many and diverse. They include: 1) research on human cells; 2) production of vaccines or antivirals; 3) toxicological studies; 4) drug development; 5) protein manufacturing (using the cells as hosts for production of various human-specific factors); 6) liver cell therapies; 7) liver gene therapies; and 8) bioartificial livers that can be used in research, toxicological and antimicrobial studies, protein manufacturing, or clinically as a liver assist system. Considering the ability of the primitive and proximal hepatic stem cells to differentiate into hepatocytes and biliary cells, the cells of the present invention can be used both for hepatic or biliary fates depending upon the microenvironment in which they are placed.

The availability of human hepatic progenitor cells (all four categories) will enable much more extensive research on human cells, will facilitate the development of successful forms of liver cell and gene therapy, and should enable the development of human bioartificial livers for use both in research and as clinical assist devices. At present, the limited supply of healthy human tissues precludes clinical programs in liver cell therapy or in human bioartificial livers. The progenitor cell populations should have sufficient expansion potential to overcome, or at least greatly alleviate, that limited supply. Moreover, these cells and their immediate descendents show preferential survival to ischemia, both cold and warm, relative to that observed with mature liver cells, meaning that livers that cannot be used for liver transplantation or for producing healthy mature liver cells are sources of the progenitor cells.

The invention is illustrated by the following non-limiting examples.

Example 1

Preparation of Hepatic Cell Suspension from Fetal Tissue

Liver tissue was obtained from fetuses between 18-22 weeks gestational age obtained by elective terminations of pregnancy. The samples of liver tissue were shipped overnight in RPMI 1640 supplemented with 10% fetal bovine serum.

Tissue volume ranged from 2 to 12 mL after a preparatory wash in cell buffer (RPMI supplemented with bovine serum albumin (BSA Fraction V, 0.1%, Sigma, St. Louis, Mo.), selenious acid (300 pM), and antimicrobial mix, AAS (Gibco BRL/Invitrogen Corporation, Carlsbad, Calif.). Liver tissue was subdivided as necessary into fragments of 3 mL or less for digestion in 25 mL of cell buffer containing type IV collagenase and deoxyribonuclease (Sigma, St Louis, Mo.; both at 6 mg per mL). Incubation was conducted at 32° C. with frequent agitation for 15-20 minutes and resulted in a homogeneous suspension of cell aggregates. The suspension was then passed through a 40 gauge sieve and spun at 1200 RPM for five minutes before resuspension in a calcium-free solution of Hanks buffered salt solution, supplemented with EGTA (0.2 mM, Sigma), Hepes (20 mM, Boehringer Mannheim), BSA (0.1% Sigma), DNase (0.01% Sigma) and termed HBSS mod.

The enzymatically digested suspension comprises hemopoietic and hepatic subpopulations. An antigenic profile of the enzymatically digested suspension is shown in Table 1 with the AFP-expressing cells being 6-9% of the original cell suspension (FIG. 12) and with a comparable percentage of albumin-expressing cells along with a significant contamination of hemopoietic cells (see the percentages of CD45 and glycophorin A expressing cells in Table 1). If the original cell suspension is cryopreserved, some cells, such as the erythroid cells, are lost enriching the albumin and AFP-expressing cells to 15-20% (Table 1). However, the most striking enrichment occurs with the partial enzymatic digestion with collagenase to yield aggregates of parenchymal cells that are then separated from the non-parenchymal (floating) cells by repeated low speed centrifugation as described below and yields a cell suspension that is more than 80% albumin and AFP-expressing cells (Table 1).

Hematopoietic cells (mostly erythrocytes and erythroblasts) and floating non-parenchymal cells were then separated from the parenchymal cell fraction by repeated slow speed centrifugation at 30 g (300 RPM) for five minutes in HBSS mod. The pellet was resuspended and re-centrifuged in 40 mls of HBSS mod until the color showed minimal contamination with red blood cells. Normally, as reported by others, this required four or five cycles of centrifugation and resuspension [14, 15]. Clumping was minimized by a second-round of enzymatic digestion in fresh collagenase solution followed by sieving through a 50 µm nylon mesh and return of the cells to a calcium-free buffer.

The resulting cell suspension was washed twice then 5 mL aliquots, each containing about 2×107 cells, were layered onto 5 mL of Ficoll Hypaque (Amersham Pharmacia, Piscataway, N.J.) in 50 mL Falcon tubes and spun at 3000 RPM for 20 minutes. Cells from the interface and pellet were resuspended separately in plating media (RPMI supplemented) and an aliquot of each was stained with trypan blue for enumeration and viability assessment with a hemacytometer. Cell viability was routinely higher than 95 percent. The low-speed centrifugation method for enrichment of the parenchymal cells eliminated the hemopoietic constituents leaving a cell suspension that was approximately 80% AFP-expressing cells. The majority of the AFP-expressing cell are proximal hepatic stem cells given that they express AFP, albumin and CK19 but not hemopoietic markers (Table 1).

TABLE 1

Flow Cytometric Analyses on Freshly isolated Fetal Liver Cells

| Marker | Location | % Positive in Original Cell Suspension, OCS (% in C-OCS) | % Positive in Enriched Parenchymal Preparation |
|---|---|---|---|
| AFP | Cytoplasmic | 6.4 ± 0.8% (~15-20%) | 75.5% |
| Albumin | Cytoplasmic | 9.3% (~15-20%) | >80% |
| CD45 | Surface | 1.4% ± 0.4 | |
| Glycophorin A | Surface | >50% (37.5 ± 9%) | Negligible |
| CD34 | Surface | (2.7 ± 0.5%) | |
| CD38 | Surface | (1.2 + 0.3%) | |
| CD14 | Surface | 3.0± | |
| CD 117 (c-kit) | Surface | ~1% | |
| Ep-CAM | Surface | n.d. | |
| CD146 | Surface | n.d. | |
| N-CAM | Surface | n.d. | |
| CAM-5.2 | Surface | n.d. | |
| PE-CAM | Surface | n.d. | |
| CD133 | Surface | n.d. | |
| Cytokeratin 19 | Cytoplasmic | n.d. | |
| Cytokeratin 8/18 | Cytoplasmic | n.d. | |

OCS = original cell suspension;
C-OCS = original cell suspension was cryopreserved in a proprietary buffer. The cells were later thawed and then analyzed for expression of the markers. A number of cells, especially the erythroid cells (enucleated subpopulation) do not survive cryopreservation.
Parenchymal preparation = after elimination of erythroid cells and other floating, nonparenchymal cells by repeated centrifugation at low speed spins;
n.d. = not done Example 2

Preparation of Hepatic Cell Suspension from Adult Tissue

A human liver was obtained from an authorized organ procurement organization. The donor was a 13 year old female who had suffered brain death. The liver was digested using a whole-organ perfusion technique. The single-cell suspension was then fractionated to obtain viable cells using a 2-step Optiprep gradient (9-12.5%) on a Cobe 2991 cell washer. Live cells were then separated from residual dead cells by mixing equal volumes of the 9% (band 1) and 12.5% (band 2) fractionated cells individually with 25% Optiprep for further fractionation on the Cobe 2991. Based on flow cytometric analysis of forward and side scatter parameters, the cellular composition of band 1 and band 2 appeared similar. The cells were cryopreserved.

Example 3

Colony Formation from Adult Human Liver Cells

To assess the presence of liver stem cells by colony formation, cells from Example 2 were thawed and plated at a density of 12,500 live cells/well on a 6 well plate, in triplicate, onto a STO-5 feeder layer. The tissue culture medium used was DMEM F12 containing penicillin/streptomycin (50 U/ml/50 ug/ml), bovine serum albumin (0.2% w/v), transferrin (10 ug/ml), free-fatty acids (7.6 uEq/L) nicotinomide (4.4 mM), selenium (3×10(−8) M), copper (1×10(−6) M), 2-mercaptoethanol (5×10(−5) M), L-glutamine (2 mM), insulin (5 ug/ml), hydrocortizone (10(−7) M), with (+EGF) or without (−EGF) the addition of epidermal growth factor.

Cells were cultured for 5 days, fixed, and colonies counted as visualized by light microscopy. No colonies were observed in any wells of unfractionated cells. This may be due to inhibitory effects of dead or dying cells, or some other component of the cell preparation prior to centrifugation on Optiprep gradient. However, colonies were observed from both the band 1 and band 2 cells fractions. 8 total colonies were observed in the 3 wells containing cells from band 1 (4 from +EGF medium, 4 from −EGF medium), and 13 total colonies were observed in the 3 wells from band 2 (11 from +EGF medium, 2 from −EGF medium). The overall frequency of colony forming cells calculated for this experiment was 0.03%.

Example 4

Figure 14A:
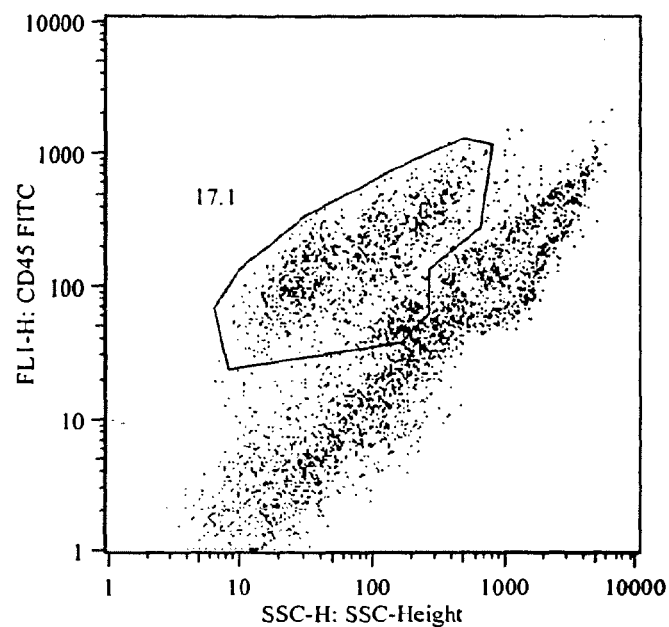
Figure 14B:
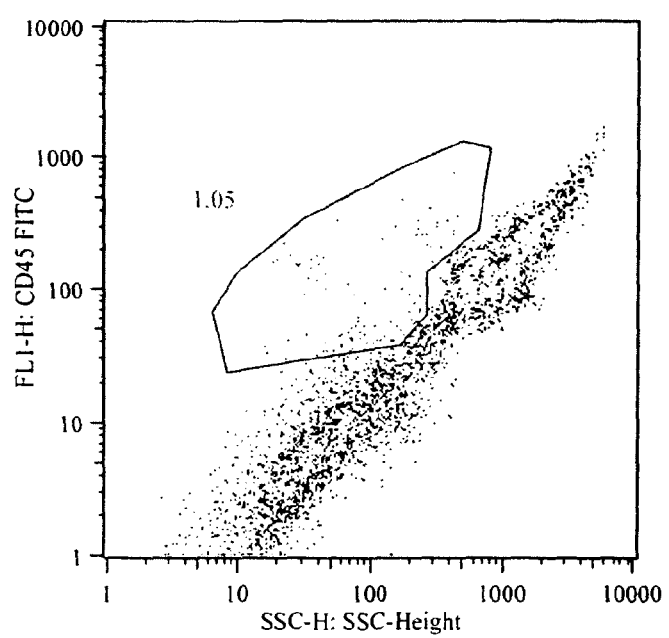
Figure 19:
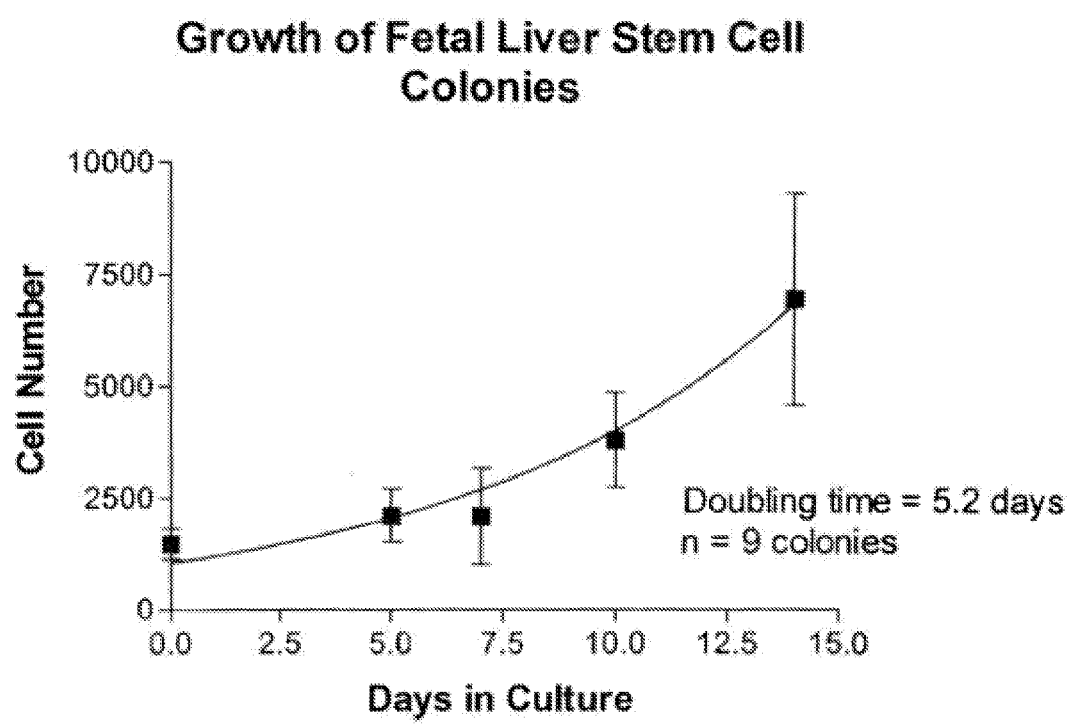
FIG. 19 depicts the growth curve of 9 stem cell colonies from 3 livers cultured on plastic over a 3 week period. Growth measurements started after 12 days in culture. The curve shows that the cells grow with a doubling time of 5.2 days.

Co-Expression of Albumin, CD133, and Ep-CAM in a Subpopulation of Adult Human Liver Cells Cells were isolated from donor livers essentially as described in Example 2. The presence of cells expressing the CD45 cell surface antigen, or Leukocyte Common Antigen, a tyrosine phosphatase expressed widely on white blood cells (leukocytes) was assessed by fluorescence activated cell sorting (FACS) using an anti-CD45 monoclonal antibody. Approximately 17 percent of the cells were CD45-positive (FIG. 14A). The CD45-positive cells were depleted by magnetic cell sorting using anti-CD45 monoclonal antibody and super-paramagnetic MACS MicroBeads and the autoMACS, an automated bench-top magnetic cell sorter. Both the magnetic-bead labeled antibody and the instrument were supplied by Miltenyi Biotec. CD45-positive cells could also be depleted by "panning", fluorescence activated cell sorting, or other modes of negative immunoselection. After depletion, the fraction of CD45-positive cells remaining in the liver cell preparation was reduced to approximately 1 percent (FIG. 14B). Depletion of CD45-positive cells facilitates the further analysis of antigens on hepatocytes and hepatic progenitor and stem cells. It also should facilitate the isolation of enriched populations of these cells.

a. Albumin

After depletion of CD45-positive cells, a sample of the liver cells was analyzed for expression of human serum albumin. Cells were fixed with paraformaldehyde, permeabilized by treatment with 0.2% Triton X-100 detergent, and stained by sequential incubation with a mouse $IgG_1$ monoclonal antibody to human albumin, and affinity-purified goat antibodies against mouse immunoglobulin $G_1$ ($IgG_1$) labeled with the fluorescent dye A647. Background staining and autofluorescence of the cells was determined by using a purified mouse myeloma protein (also an $IgG_1$), with no specific binding activity to human antigens, in place of the anti-albumin monoclonal antibody. Approximately 97.5 percent of the cells were albumin-positive (FIG. 15A). The gating for positive staining (red outline) was determined by comparison to the mouse myeloma protein control (not shown).

Measurement by FACS of forward light scatter and side light scatter can be used to characterize cellular populations. The forward and side scatter are primarily functions of cellular size and intracellular structural complexity, respectively. As shown in FIG. 15B, the albumin-positive cellular population from adult human liver comprises a majority class of cells with relatively high forward (FSC) and side scatter (SSC). Analysis of size and morphology, as well as additional biochemical and antigenic markers (not shown), shows that these cells have properties consistent with mature, small hepatocytes (average size approximately 18-22 micrometer diameter). The largest hepatocytes (approximately >30 micrometer diameter) from normal adult human liver apparently are under-represented in our preparations, probably because of greater susceptibility to death during the period between harvesting of the organ and perfusion, and/or greater susceptibility to damage during the isolation procedure. However, FIG. 15B also shows that, in addition to the mature, small hepatocytes, many cells characterized by lower forward and side scatter also express albumin. The few (approximately 2.5 percent) albumin-negative cells in the preparation almost exclusively show very low forward and side scatter (FIG. 15C). These may be dead cells, or very small cells such as late stage precursors of red blood cells.

b. CD133

The antigen CD133 (AC133) is a cell surface glycoprotein of 120 kilodaltons that has five transmembrane domains. The protein is similar or orthologous to the mouse protein prominin. The human CD133 antigen originally was identified on a subset of early progenitors, including stem cells, in the lineage of blood-forming (hematopoietic) cells. Certain other immature cells express CD133, including developing epithelium in human embryos (week 5), endothelial cell precursors, and neuronal progenitors or stem cells. Expression of CD133 also has been reported on certain human tumors and tumor-derived cells lines, such as retinoblastomas and the colon carcinoma line CaCo-2. The protein is found concentrated preferentially in plasma membrane profusions such as microvilli. When found on epithelial cells, it localizes preferentially to the apical, but not to the baso-lateral membrane surface. Previous studies, in particular by immunohistochemistry, have failed to demonstrate CD133 protein expression in adult human epithelial tissue, despite the presence of detectable messenger RNA for the protein in many human tissues, including adult liver.

We used staining with a fluorescent-labeled monoclonal antibody and analysis by FACS to search for cells expressing the CD133 antigen in our CD45-depleted adult human liver cell preparations. Surprisingly, in light of the prior negative reports, we observed that a majority of the CD45-depleted liver cells (see FIG. 14B) show positive staining for CD133. FIG. 16A reveals approximately 58 percent CD133-positive cells in a preparation from the liver of a juvenile (two year-old) individual. The presence of a substantial population of CD133-positive cells, including cells of the size of small mature hepatocytes, has been observed in cell preparations from additional individuals, including adults. The CD133-positive population (upper box in FIG. 16A) comprises roughly half of the cells in the preparation identified as mature (small) hepatocytes on the basis of side light scatter (FIG. 16A) and forward light scatter (not shown). It also comprises many cells that are smaller than and morphologically distinct from mature hepatocytes, as judged by light scatter.

Magnetic cell sorting can be used to positively select the liver cells that express CD133. FIG. 16B shows enrichment of CD133-positive cells to approximately 75% of recovered cells after one cycle of magnetic sorting utilizing the autoMACS instrument (Miltenyi Biotec). The use of higher amounts of antibody-coupled MACS MicroBeads and adjustment of the sorting conditions should permit the isolation of more highly enriched CD133-positive cell populations with nearly quantitative yield. {Also note that other methods of positive immunoselection can be used to enrich for the CD133-positive cells}. As judged by side scatter (FIG. 16B and forward scatter (not shown), the enriched CD133-positive cells comprise all of the CD133 subpopulations identified in the CD45-depleted liver cell preparation.

c. Ep-CAM

The epithelial cell adhesion molecule (Ep-CAM, also known as GA733-2, CO17-1A, EGP40, KS1-4, and KSA) is a glycoprotein implicated in homophilic, calcium ion-independent cell-cell adhesion. The protein is expressed in many human epithelial tissues, and appears to be up-regulated substantially in proliferating epithelial cells, including tumor cells. C. J. de Boer and colleagues reported that in 8-week embryonic human liver most hepatocytes express detectable Ep-CAM protein [de Boer C J, van Krieken J H, Janssen-van Rhijn C M, Litvinov S V. (1999). "Expression of Ep-CAM in normal, regenerating, metaplastic, and neoplastic liver," Journal of Pathology 188:201-6]. By contrast, in normal adult human liver they failed to detect Ep-CAM expression in hepatocytes, and reported that only bile duct epithelial cells stain positively for this antigen. Finally, the antigen was detected in cells identified as hepatic precursors in situations in which liver regeneration and repair was induced by biliary cirrhosis, and in cells of certain liver tumors, particularly cholangiocarcinomas.

By FACS analysis we consistently detect a minor population of Ep-CAM-positive cells in unfractionated human liver cell preparations from both juveniles and adults. The Ep-CAM-positive population comprises approximately 0.4 to 2.5 percent of the cells. As shown in FIG. 17 Ep-CAM-positive cells also can be observed in liver cell populations after depletion of >95 percent of CD45-positive cells. FIG. 17B shows the Ep-CAM-positive cells from one such human liver preparation (0.57 percent in the region of the plot gated as shown by the red outline, as compared to 0.15 percent in the same gated region for a control antibody that does not stain any known human antigen, FIG. 17A; thus approximately 0.57–0.15=0.42 percent of the cells are Ep-CAM-positive). Double label analysis (data not shown) demonstrates that the vast majority of the Ep-CAM-positive cells in the CD45-depleted population are, as expected, CD45-negative. However, it appears that some (roughly 1 percent) of the CD45-positive cells in our human liver preparations also express Ep-CAM (data not shown).

d. Co-Expression of Ep-CAM, CD133, and Albumin

We searched for liver cells from adult human liver that express both Ep-CAM and CD133. Cells were incubated with monoclonal antibodies to CD133 and Ep-CAM, each directly conjugated with a different fluorochrome. As shown in FIG. 17C, approximately 42 percent of the cells in this particular CD45-depleted adult human liver cell preparation stained detectably for CD133. (The somewhat lower degree of CD133 staining here than in the experiment shown in FIG. 16A may result from actual differences between liver cell preparations from different donors, as a consequence of age or other variables, or from unidentified variations in experimental technique). Among cells in the population that stained strongly for Ep-CAM (shown within the red boundary in FIG. 17B), approximately 70 percent also stained positively for CD133 (FIG. 17D). Thus, in this particular liver preparation approximately 0.3 percent of the total CD45-negative cells co-expressed Ep-CAM and CD133.

The cell preparation used for the experiment shown in FIG. 17 was identical to that used in the analysis of albumin expression shown in FIGS. 14 and 15. As noted above, approximately 97.5 percent of the cells in the CD45-depleted cell population stained positively for albumin, and the few albumin-negative cells displayed a distinctive pattern of low forward scatter and side scatter. As shown in FIG. 17E, virtually all (approximately 99.5 percent) of the cells found to co-express CD133 and Ep-CAM showed forward scatter and side light scatter characteristic of the albumin-positive cells; they fall entirely outside of the bounded region of the plot of forward scatter versus side scatter that is contained all of the albumin-negative cells (see FIG. 15C). Thus, the postnatal human liver cells that co-express Ep-CAM and CD133 also express human serum albumin.

e. Co-Enrichment of CD133 and Ep-CAM Expressing Cells

As shown in FIG. 16B, positive immunoselection such as magnetic cell sorting allows the enrichment of CD133-positive cells from human liver cell preparations. We assessed cells in the starting population (already CD45-depleted) and the CD133-enriched preparation for the expression of Ep-CAM. FIG. 17A shows that at least 1.1 percent (deliberated gated tightly) of the starting population expressed Ep-CAM. After enrichment of CD133-positive cells, the resulting population (FIG. 5B) contains at least 4.5 percent Ep-CAM-positive cells. This confirms the coexpression of CD133 and Ep-CAM in a subpopulation of cells from adult human liver, and demonstrates that these cells can be enriched by positive immunoselection. Analysis of forward and side scatter (as in the experiment of FIG. 17) by the cells that co-express the two surface antigens again shows that nearly 100 percent of these cells also must be albumin-positive.

The adult human liver cells described above co-express albumin, a prototypical marker of the hepatocyte lineage, together with either CD133, or Ep-CAM, and therefore have the same is the same phenotypic profile of certain hepatic stem cells from human fetal liver described herein. Moreover, the adult human liver cells described herein are liver cells of size smaller than mature hepatocytes (even "small hepatocytes" of 18-22 micron diameter). Taken together with the finding that adult human liver contains cells capable of forming colonies under conditions that operationally define hepatic stem cells (i.e., in serum-free medium with STO feeder cells), the co-expression of albumin, Ep-CAM and CD133 demonstrates the presence of such stem cells in adult liver. Methods of positive immunoselection described herein may be used to isolate cells that simultaneously express the two surface markers, Ep-CAM and CD133 in order to obtain highly enriched populations of hepatic stem cells from human liver, including tissue derived from a child or an adult.

Example 5

Primary Cultures of Proximal Hepatic Stem Cells on STO Feeder Layers

Most of the liver progenitors, with the exception of the primitive hepatic stem cells, do not survive for long being co-cultured with embryonic liver stromal feeders; feeders from neonatal livers, adult livers, or diverse adult tissues were not successful (Sigal et al, 1994; Brill et al, 1995; Sigal et al, 1995; (Brill S, Zvibel I, and Reid L M. Expansion conditions for early hepatic progenitor cells from embryonal and neonatal rat livers. Digestive Diseases and Sciences 44:364-371, 1999). The embryonic liver stromal feeders can be replaced by STO cells, an embryonic stromal cell line, used as routine feeders for embryonic stem cells and found to support clonogenic expansion of freshly isolated, normal rodent hepatic stem cells and diploid adult rat liver cells (Kubota and Reid, 2000). These conditions were found essential also for the all of the progenitors from human fetal liver, with the exception of the primitive hepatic stem cell that would expand with and without the feeders (Moss et al submitted). The STO feeders have also proven successful for hepatic progenitors from neonatal and adult human livers (Ludlow, et al, in preparation). The factors supplied by the embryonic stromal feeders and essential for the progenitors are not known.

STO Feeders originally from ATCC were expanded from stock cells in 75 cm flasks in DMEM/F12 (Gibco/BRL/InVitrogen Corporation, Carlsbad, Calif.) supplemented with 10% fetal bovine serum, FBS (Hyclone, Logan, Utah) and 1% DMSO (Sigma, St. Louis, Mo.). After three passages to provide nine confluent flasks, the cells were treated for 2 hours with 10 µg/mL mitomycin C (Sigma, St. Louis, Mo.; also, Biomol, Plymouth Meeting, Pa.) to induce cell cycle arrest and washed twice with culture medium. The cells were trypsinized and resuspended in cryopreservation medium (50% DMEM/F12, 40% FBS, 10% DMSO) before freezing in 1 mL aliquots of $5 \times 10^6$ cells and stored at $-80°$ C. Feeders were prepared by seeding $6 \times 10^4$ thawed cells/cm$^2$ onto culture plates pre-coated with 0.1% gelatin (Sigma, St. Louis, Mo.). Detailed protocols described in [16] are incorporated herein by reference.

Cells passaged onto STO cells were cultured in a serum-free, hormonally defined medium (HDM) comprising RPMI 1640 (GIBCO/BRL/InVitrogen Corporation, Carlsbad, Calif.) supplemented with 0.2% bovine serum albumin (Fraction V Fatty acid free, Sigma, St. Louis), insulin (5 µg/ml), transferrin/Fe (10 µg/ml), selenium ($3 \times 10^{-8}$M), 2 mercaptoethanol ($5 \times 10^{-5}$ M) a complex mix of free fatty acids (7.6 µEq; [16, 17]), hydrocortisone ($10^{-7}$ M), glutamine (2 mM), nicotinamide (4 mM), and AAS (penicillin, 1000 µg/mL, streptomycin 100 µg/ml, and amphotericin B 250 ng/mL, Sigma). Preferably, neither cytokines classic hepatic growth factors (e.g. epidermal growth factor, EGF, hepatocyte growth factor, HGF, nor insulin-like growth factors, IGFI and IGFII) were used.

Figure 6:
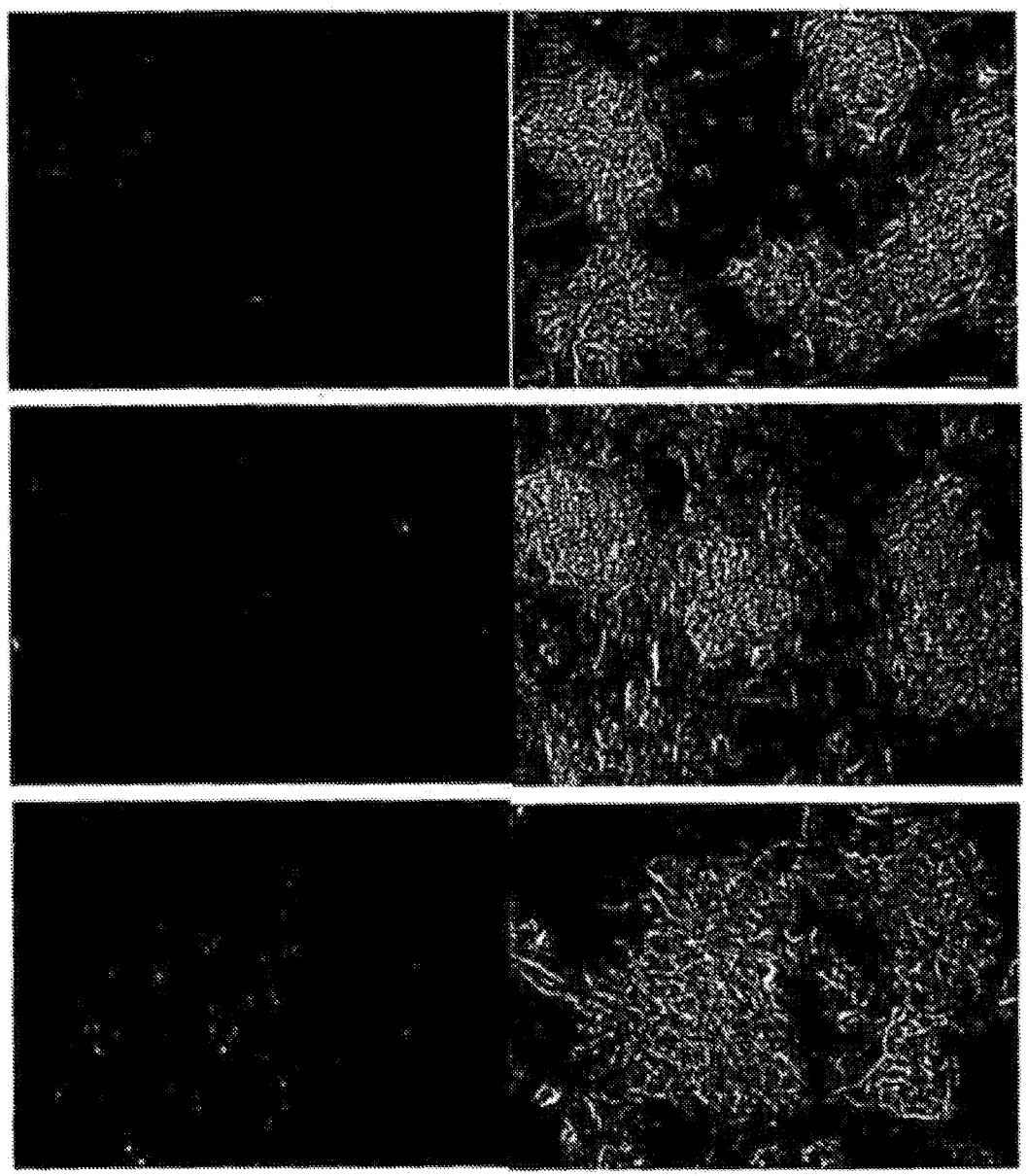
FIG. 6 demonstrates a primary culture of proximal stem cells after 7 days on a STO feeder layer staining for albumin (row 1), alpha-fetoprotein (row 2), and CK19 (row 3).
Figure 7:
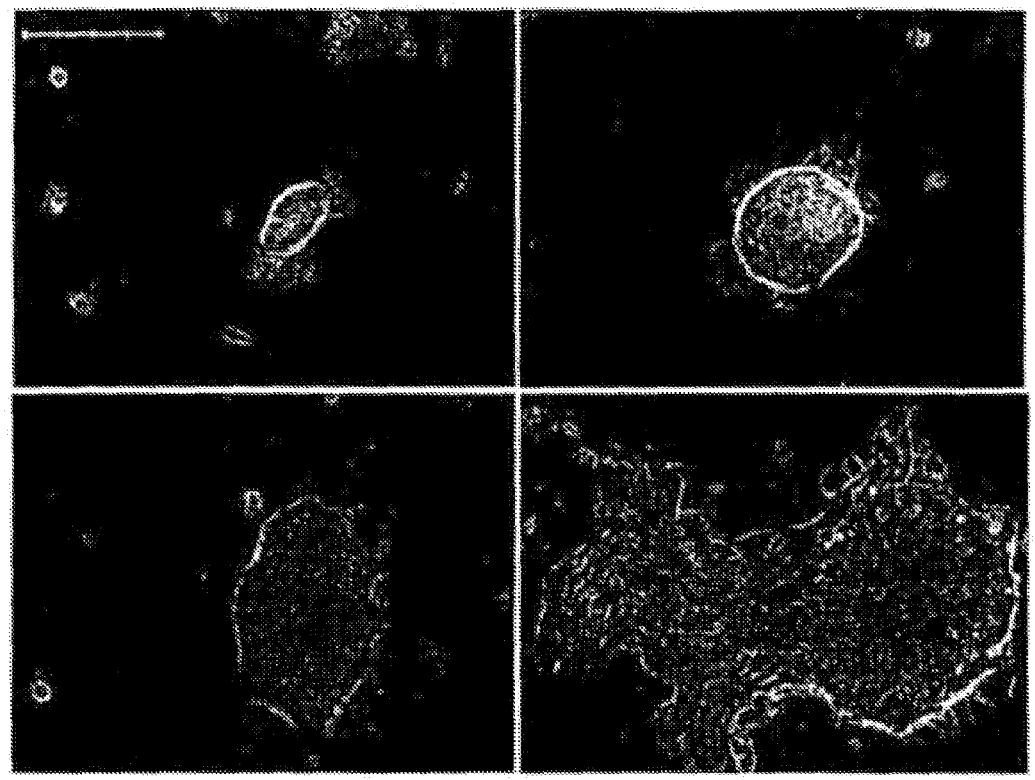
FIG. 7 demonstrates the development of a colony cell removed from plastic culture and plated onto a STO cell feeder layer.

Primary cultures of dispersed, enriched parenchymal cells from Example 1 were plated onto a STO feeder layer produced stable aggregates of proximal hepatic stem cells that express albumin, AFB and CK19. Typical cells staining for albumin, AFP, and CK19 are shown in FIGS. 6a-6c. These cells were also positive for CK8/18. Unlike cells cultured on a plastic substratum as described in Example 6, the proximal hepatic stem cells seeded onto STO feeders retained a consistent morphology and maintained AFP expression for several weeks. Since these conditions support both proximal hepatic stem cells and more differentiated cells including diploid adult liver cells ([7]) co-culture with STO feeders proved unsuitable for selection of truly primitive colony-forming cells.

Example 6

Selection of Primitive Hepatic Stem Cells

The enriched parenchymal cell suspension of Example 1 was plated at a density of 2000-5000 cells/cm$^2$ onto tissue culture plastic in a serum-free medium supplemented with lipids, insulin and transferrin/Fe (HDM). For the first 12 hours after plating, the medium contained 10% FBS to promote cell attachment after which the cultures were maintained serum-free. Media changes occurred at three-day intervals.

Figure 2:
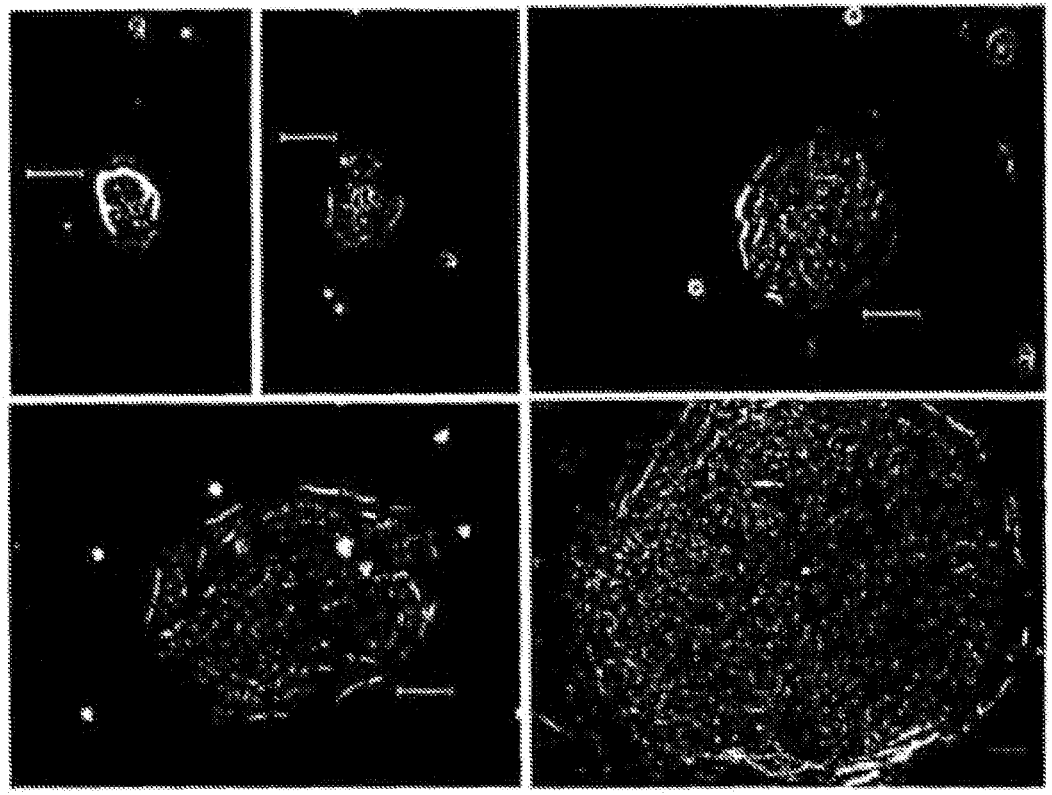
FIG. 2 demonstrates colony formation on plastic culture from Day 5 to Day 14.

Immediately after attachment the predominant cells present in culture were proximal hepatic stem cells and committed progenitors, aggregates of cells with a classic parenchymal cell morphology, and with expression of albumin, AFP and/or CK19; the proximal hepatic stem cells will demonstrate albumin, AFP and CK19 (FIG. 2a). After several days, the proximal hepatic stem cells and committed progenitors ceased expressing AFP and were replaced by solitary, motile cell types with a myofibroblastic appearance that dispersed into the dish. In addition to proximal hepatic stem cells, several other cell types were present in culture, some solitary, some forming extensive confluent monolayers, while others formed discrete round cell groupings. Amongst these types of cells, positive staining for albumin was observed only in the proximal hepatic stem cells, the committed progenitors, and in circular, tightly aggregated colonies, the primitive hepatic stem cells, which appeared in culture concurrently with the gradual demise of the proximal hepatic stem cells and the committed progenitors.

Colony formation showed a predictable sequence of events. An initial wave of colonies appeared within the first few days in culture and appeared to arise from aggregations of pre-existing cells (FIG. 1b). However, after 5-7 days, a new wave of colony formation started from solitary cells scattered throughout the culture dish. These colonies were first recognizable as groups of 4-8 small, dark, tightly compacted cells with lamelipodia at the periphery that formed a narrow continuous fringe (FIG. 2a). The colonies expanded into extensive groupings of tightly aggregated, rounded cells 8-10 µm in diameter (FIG. 2b-2e). The general appearance of these late-forming colonies is distinct from colonies that form in the first days of culture, which were composed of larger cells, and from the initial aggregations of proximal hepatic stem cells that constitute the main parenchymal cells in fetal liver.

The primitive hepatic stem cells grew well on tissue culture plastic in the HDM and achieved diameters of up to 1 cm after several weeks in culture. Numerous colonies were removed selectively and dispersed by trypsinization to yield an average cell number per colony that ranged from 1000 cells for colonies 3 mm in diameter to 15,000-20,000 in large colonies with diameters of 1 cm.

Figure 3:
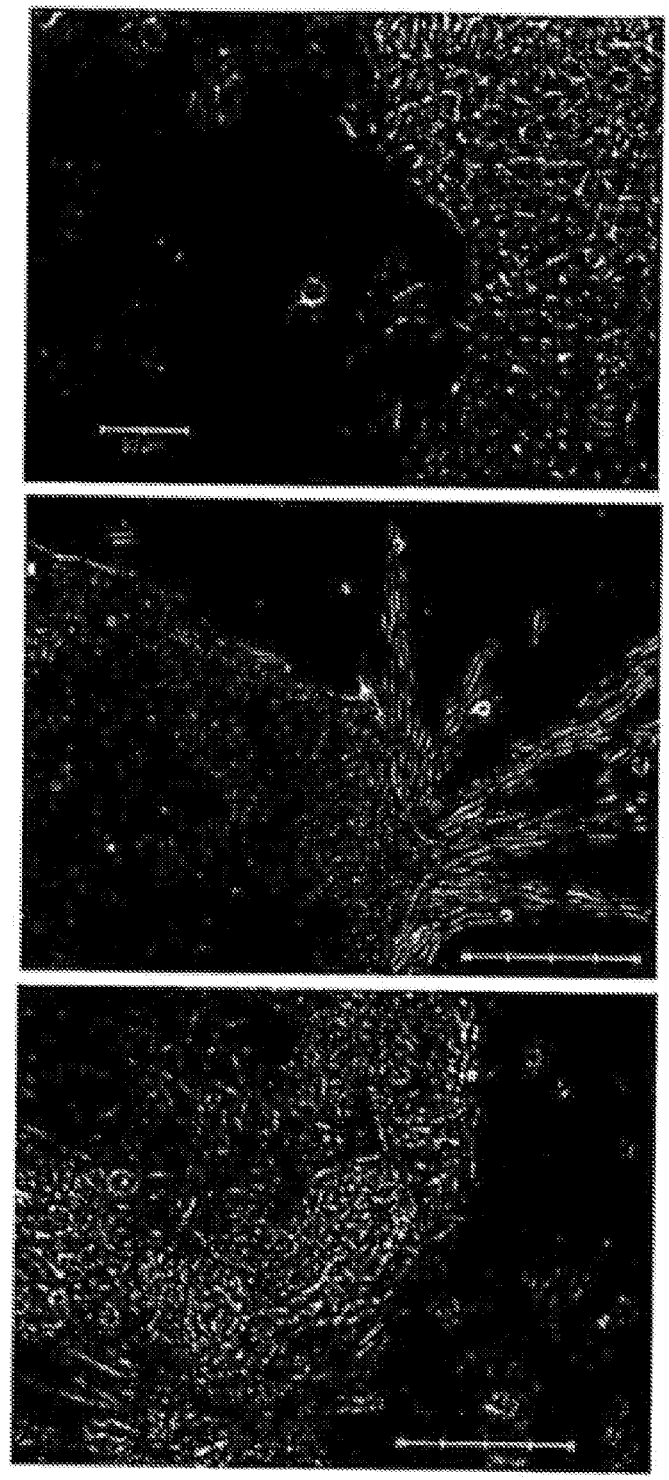
FIG. 3 demonstrates colony behavior on plastic culture.

Typically, the outermost cells of the colonies converted into a flattened phenotype that became separated from the colony to form solitary, large diameter cells that dispersed throughout the culture dish (FIG. 3a). In other colonies, cells at the perimeter assumed an elongated, fibroblastic appearance that initially wrapped closely around the circumference of the colony, perhaps tightly associated mesenchymal cells (FIG. 3b). These cells also migrated away from the colonies as isolated, fusiform cells. These dispersed cells remained highly proliferative and often became the predominant cell type in culture, forming a tightly packed layer that extended throughout the dish. The colonies were surrounded but not overgrown by this cell layer, though a transitional zone formed at the margin of each colony where the two cell types became interspersed (FIG. 3c).

Example 7

Antigenic Profiles of Colony Forming Cells in Plastic Culture

The antigenic characteristics of the cells cultured in Example 6 was investigated with immunocytochemical staining for markers relevant to hepatic organogenesis. Cell cultures were fixed with a 50/50 (V/V) mixture of methanol and acetone for 2 min at room temperature. Several staining regions were created on the surface of each dish with a PAP marker pen (Research Products International Corp, Mt. Prospect, Ill.) to allow multiple antibody combinations within the same culture. Non-specific binding sites were blocked by incubation with a solution of 10% goat serum (GIBCO/BRL/In Vitrogen, Carlsbad, Calif.) in PBS for 30 min at room temperature. After rinsing twice with PBS, primary monoclonal antibodies were applied to each of the staining regions (normally 0.1-0.3 mL per region) and incubated overnight. After incubation overnight at 4° C. cells were washed twice with PBS and then incubated with a secondary antibody conjugated either to Alexa 488 (1:750) or Alexa 594 (1:1250) (Molecular Probes, Eugene Oreg.). In some instances a primary monoclonal antibody conjugated to either FITC or PE was available and provided the means for double labeling by incubation with this antibody after completion of the labeling protocol with an unconjugated primary antibody.

Figure 4:
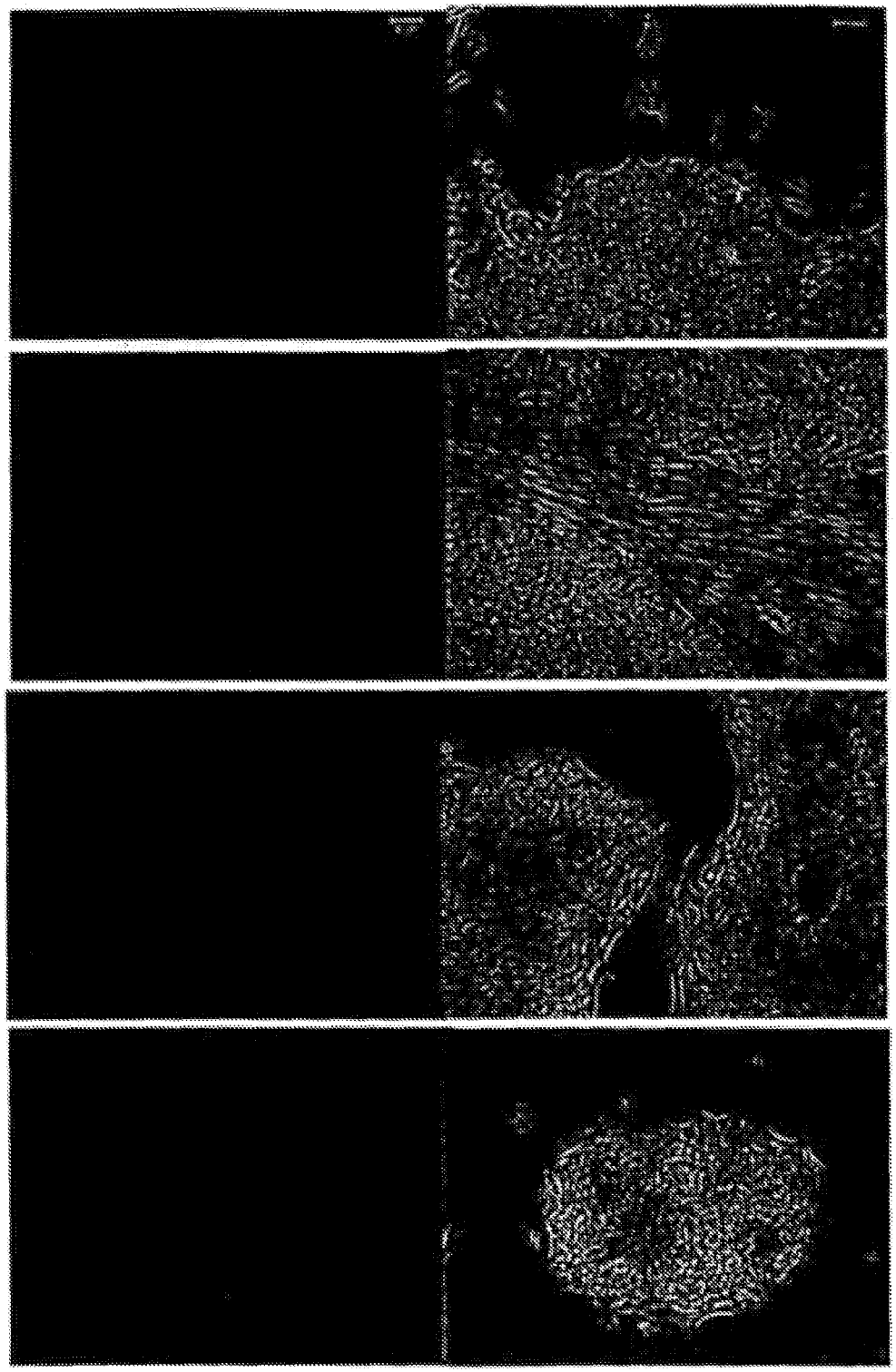
FIG. 4 demonstrates staining of colony cells on plastic for albumin (row 1), CK19 (row 2), ep-CAM (row 3) and NCAM (row 4).
Figure 5:
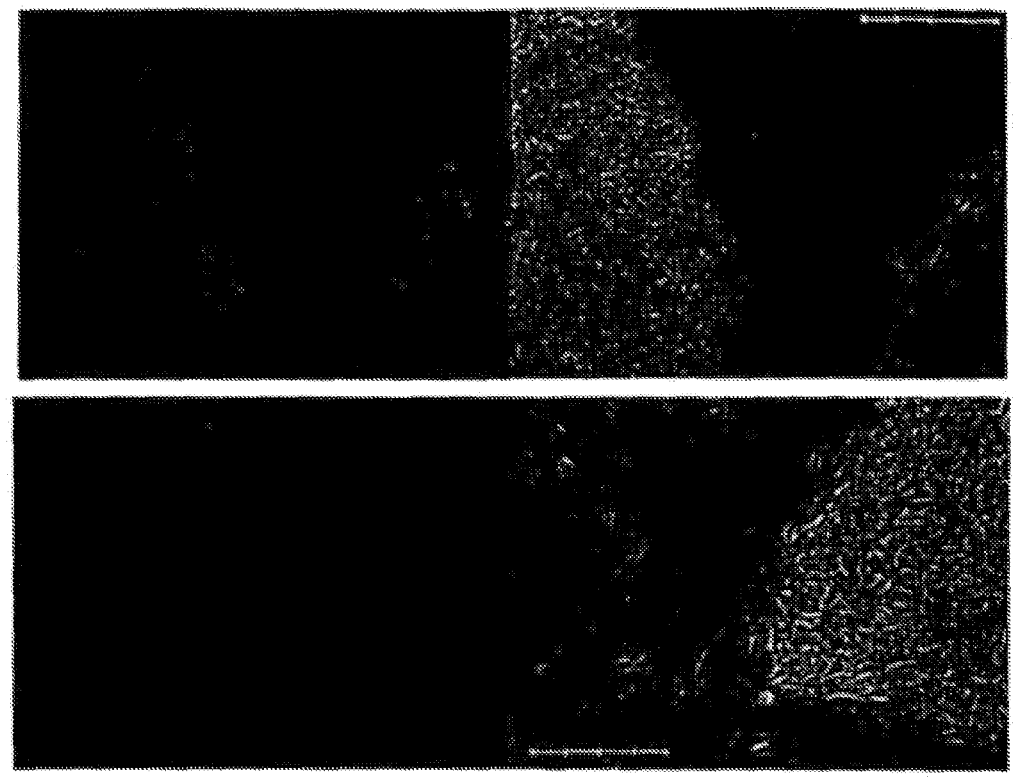
FIG. 5 demonstrates staining for colonies cultured on plastic for CD146 and CD133 (top), and AC133 (bottom).

The antigenic profile is summarized in Table 2. Colonies stained positive for a number of markers previously linked to hepatic cell types including albumin (FIG. 4a), CK19 (FIG. 4b), epCAM (FIG. 4c) NCAM (CD56, FIG. 4d) but not PECAM (CD31; data not shown). c-kit staining was seen in several colonies, generally localized to a narrow segment at the margin of colonies (FIG. 5a). Also, colonies were positive for the putative stem cell marker, CD133 (AC133, FIG. 5c). Interestingly, the cells in the transitional zone at the periphery of colonies stained positive for a recently described endothelial marker, CD146 (M-CAM, FIG. 5c), and remained positive for this protein while in the vicinity of the colonies, possibly identifying a closely associated mesenchymal cell type, possibly an endothelial progenitor. The primitive hepatic stem cells that emerged as colonies were negative for AFP, indicating that the primitive hepatic stem cells are a precursor to proximal hepatic stem cells, which in turn are precursors to hepatocyte progenitors and biliary progenitors.

TABLE 2

Phenotypes of Cultured Cells

| Phenotype | Ductal Plate Stem Cells | Proximal hepatic stem cells | Hepatocytes | Biliary Epithelia |
|---|---|---|---|---|
| Morphology under stringent conditions: tissue culture plastic and HDM | Dark, tightly packed cells, 7-10 in diameter, with "pincushion" morphology | Transiently are aggregates of small, cuboidal cells that become motile | Do not survive the stringent conditions | |
| Morphology on STO feeders and in HDM | Dark, tightly packed cells, 7-10 in diameter, with "pincushion" morphology | Stable, densely packed aggregates of cells | Diploid subpopulation flatten and have distinct cellular boundaries; polyploid cells survive but do not grow | |
| Alpha-fetoprotein | Not Expressed | +++ | Not expressed | Not expressed |
| Albumin | +++ | +++ | +++ | Not Expressed |
| CK8/18 | +++ | +++ | +++ | +++ |
| CK19 | +++ | +++ | Not expressed | +++ |
| c-Kit | +++ (cells at the periphery of the colony) | Not expressed | Not expressed | Not expressed |
| Ep-CAM | +++ | +++ | | |
| N-CAM | +++ (cells at the periphery of the colonies) | Not expressed | Not expressed | Not expressed |
| CAM-5.2 | +++ (some, not all, of the cells | Not expressed | | |
| CD 133 (AC 133) | +++ | +++ | Not expressed | Not expressed |
| CD146 | Periphery of colonies (unknown if this an associated mesenchymal cell or derived from the primitive hepatic stem cell) | Not expressed | Not expressed | Not expressed |
| PE-CAM | Not expressed | Not expressed | Not expressed | Not expressed |

Example 8

Passage of Colony Cells from Plastic Substratum to STO Feeder Cells

STO feeders were used to assess the fates of the primitive hepatic stem cells after selective passage from the plastic substratum. After 1-2 weeks in culture, colonies on plastic substratum from Example 6 were physically lifted from plastic substrata by aspiration into a 100 uL pipette under binocular magnification. Up to 50 colonies were collected in HBSS mod and then digested for up to 20 min in collagenase solution with agitation to disperse cells into suspension.

Colony forming efficiency following passage from plastic to a STO feeder layer was low, ranging between 0.5 and 1% for cells passaged at densities of 500 or 50 cells per $cm^2$. Initial attachment of passaged colony-forming cells was improved by the presence of EGF (20 ng/mL) in the plating medium. The low colony forming efficiency may have been due, in part, to the need to subject the cells to lengthy (up to 20 minutes) collagenase digestion in order to achieve single cell suspensions.

After passage onto STO feeders cells, the primitive progenitor cells merged into the STO cell layer and reappeared as tightly compacted colonies of small cells after 4-5 days in culture (FIG. 6a). The new colonies enlarged over the following weeks to produce tightly aggregated circular groupings, often with a slight thickening at the circumference (FIG. 6c). In some colonies a secondary proliferative stage occurred in which an eruption of cells occurred from a point at the edge of the colony and spread out over the STO layer, often surrounding the original colony (FIG. 6c).

Figure 9:
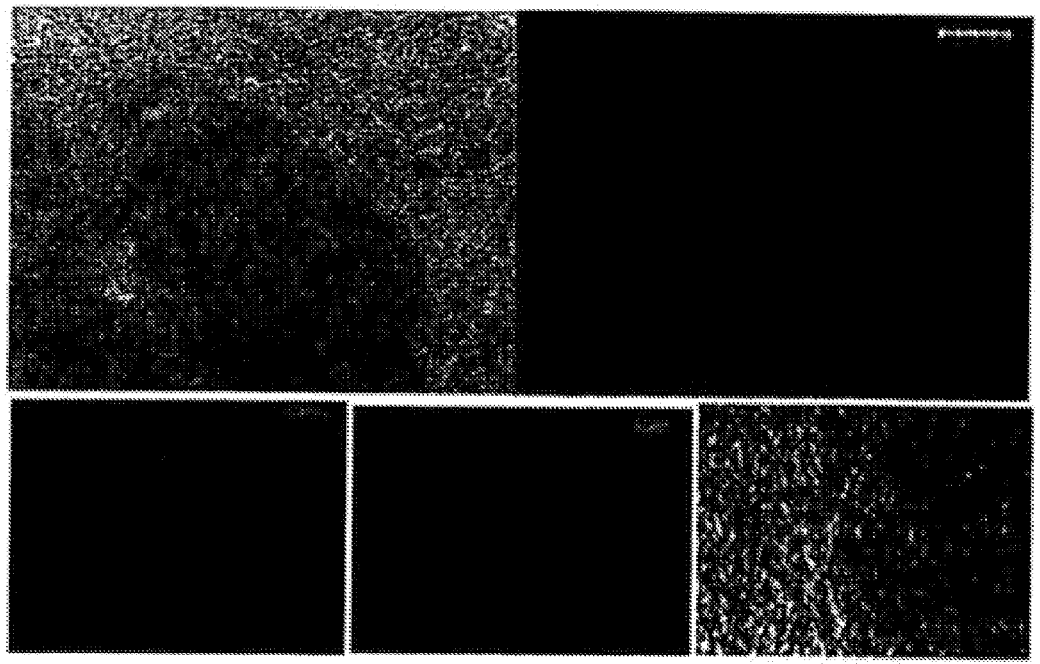

The immuno-cytochemical properties of colonies formed on STO cells were the same as those described above for colony-forming cells on plastic substrata. This includes positive staining for albumin, CK19, CK18, and CD133. As in initial colonies raised on plastic, markers such as CD146 and NCAM were most clearly expressed at the periphery of the colonies formed on STO cells. This marginal expression pattern became even more pronounced when colonies were surrounded by cells that proliferated from the primary colony. This is shown clearly for NCAM in FIG. 9 where the interface between the original colony formed from passaged cells and the secondary proliferation is marked by a band of cells with intensely positive NCAM expression. This pattern was also seen for expression of the pan cytokeratin marker CAM 5.2 and double labeling for NCAM and CAM 5.2 showed that the two markers were expressed at high levels in the same region of marginal cells (FIG. 9).

Figure 8:
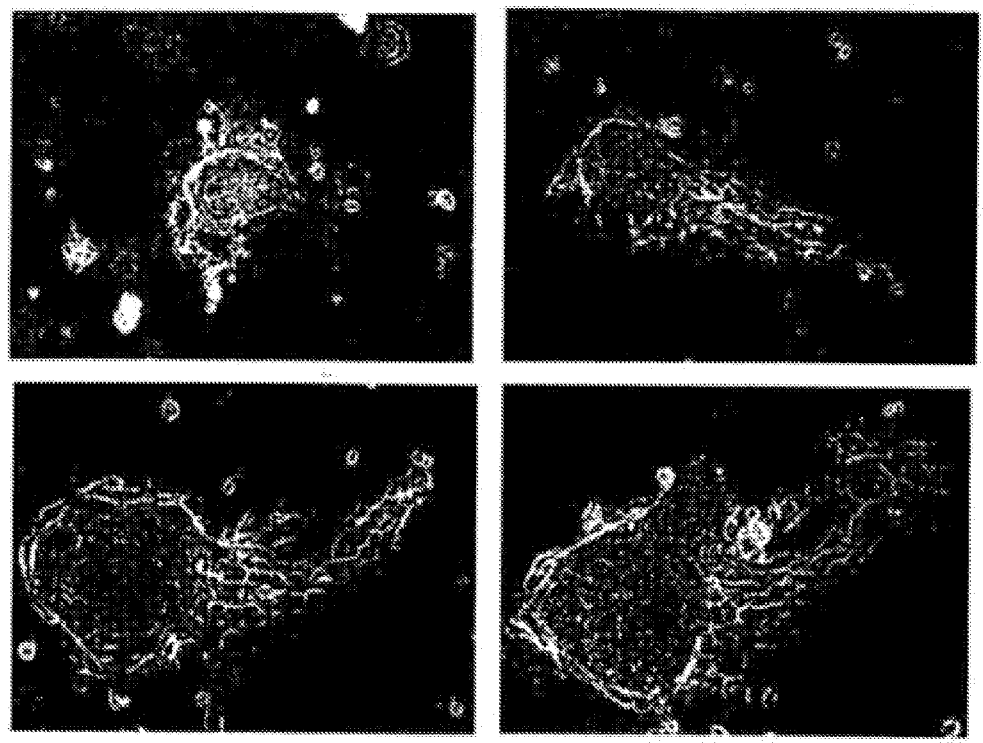
FIGS. 8-11 demonstrate eruption of cells from the colony on an STO feeder layer.
Figure 10:
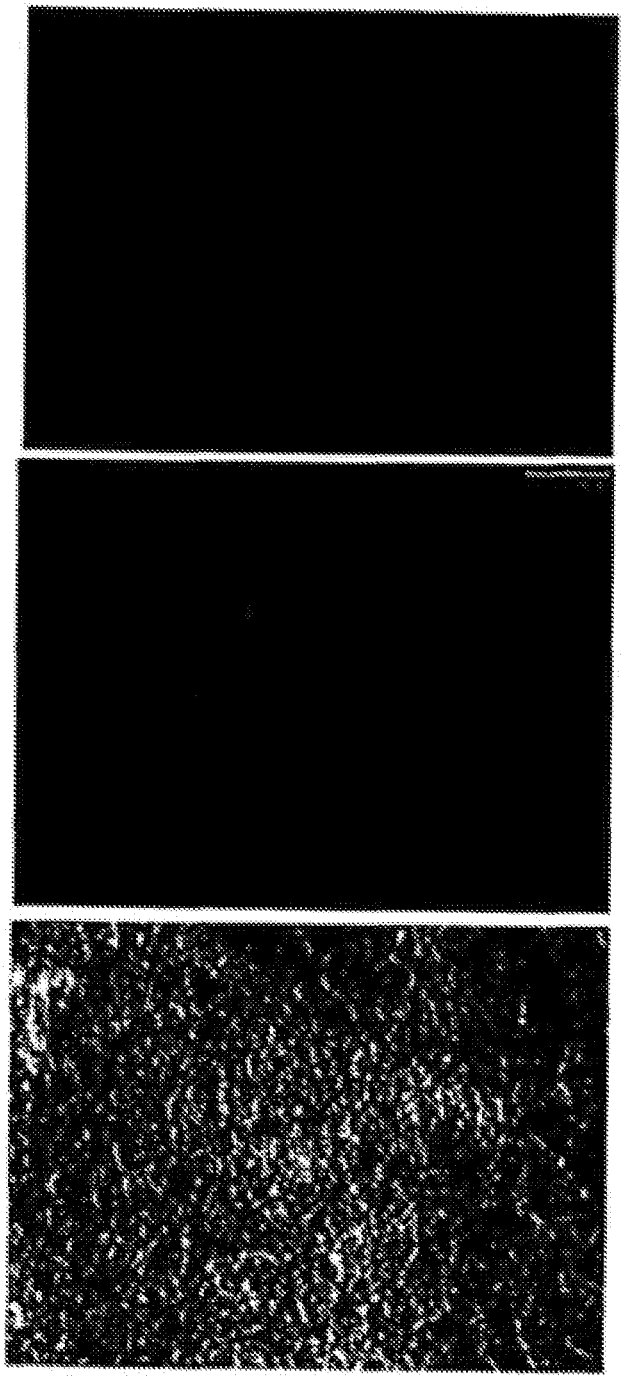
Figure 11:
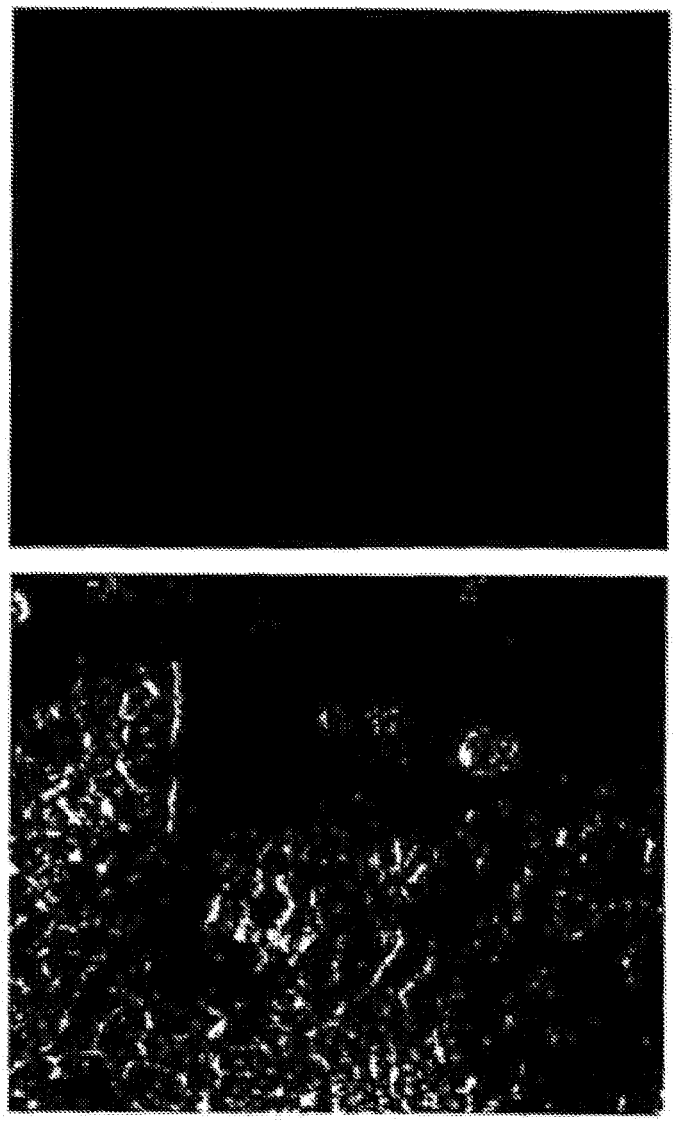

Finally, the characteristics of the erupting cell type was of interest as they emerged from the colonies in a distinct arrangement consisting of a parallel row of cells that enlarged into a branching pattern of linearly arranged cells with clear intercellular spaces (FIG. 8). When these cells had enlarged into an extensive sheet around the original cell colonies they appeared to lose the linear organization apparent at the time of emergence. However, staining for albumin revealed that the organization into rows of cells was maintained within the cell mass (FIG. 10a), and co-staining for CD146 showed that this marker is also expressed at high levels within the proliferating cell group (FIG. 10b). Perhaps of most significance in these cells is the appearance of staining for AFP at the periphery of the emerging cells (FIG. 11. This represents the first point in the ex vivo manipulations described herein that AFP expression can be linked to the progeny of the initial colony-forming cells. These data indicate that the primitive hepatic stem cells isolated in Example 6 may be used to produce hepatic committed progenitors.

Example 9

Presence of Primitive and Proximal Hepatic Stem Cells in a Liver from a Neonatal Donor A liver was obtained from a donor who was born after approximately 28 weeks of gestation and survived only one day. The period of warm ischemia between cardiac arrest and the harvesting and flushing of the donor organ was between six and seven hours. Thereafter the organ was maintained on ice for approximately twelve hours. The whole organ (wet weight approximately 100 grams) was subjected to perfusion and digestion with Liberase, and a cell suspension was prepared, essentially as for a liver obtained from a human child or adult. Non-viable cells and many red blood cells were removed by preparative centrifugation using Optiprep. However, it was difficult to determine the actual yield and percentage of viable, non-erythroid cells in the final preparation.

Portions of the recovered cells were depleted further of red blood cells by differential centrifugation, essentially as described for fetal liver cells, and then seeded in culture under conditions appropriate to determine the presence of primitive hepatic stem cells (i.e., plating in serum-free, hormonally defined medium on a tissue culture plastic substratum). Other portions of cells were plated, without further purification, under conditions to assay for proximal hepatic stem cells (i.e., plating in serum-free defined medium with STO feeder cells). Additional portions of cells were seeded on tissue culture plastic coated with Type I collagen, in serum-free, defined medium containing or lacking supplementary epidermal growth factor (EGF) at 0.5 ng/ml.

After appropriate periods of incubation, the growth of hepatic colonies was observed in all conditions tested. In the respective assays for primitive and proximal hepatic stem cells, the colony morphology and rate of growth was similar to that observed for cells cultured from human fetal liver (generally obtained after <22 weeks of gestation) cultured under the same conditions. Representative colonies were tested by immunofluorescence staining for the expression of human albumin, and were all positive for this marker.

Colonies of apparent epithelial (presumptively hepatic) morphology appeared on collagen-coated plates in the presence of EGF. Additional cells of less well-defined morphology also grew rapidly in these cultures, but have not yet been characterized in detail.

Colonies of presumptive epithelial cells also appeared on collagen-coated plates in the absence of supplementary EGF. Some of these colonies were picked individually, using a manual pipetting device, and transferred into fresh medium in 96 well plates. Cells from certain colonies have continued to proliferate in such cultures, and are being passaged as cell strains. It appears likely that these represent strains, potentially clonal, of propagable hepatic precursors, perhaps stem cells. Further characterization of expression of antigens including CD133, Ep-CAM, albumin, AFP, and CK19 will determine the relative state of differentiation of these putative hepatic stem cell lines.

Example 10

Flow Cytometry Sorting and Flow Cytometric Analyses (FACscans)

FACscans, of cytoplasmic antigens (e.g. albumin, AFP) were done with cells fixed and permeabilized with 3% paraformaldehyde prior to staining with the antisera. Cells were stained as indicated for immunofluorescence but using antibodies directly labeled with the relevant fluoroprobe (see Tables 3 and 4). The flow cytometry was performed on a Cytomation "MoFlow" flow cytometer (Fort Collins, Colo.) (FACs facility directed by Dr. Larry Arnold). The sheath fluid was unmodified HBSS. The MoFlow cytometer is capable of analysis or of sorting 40,000 cells/second, with up to 12 parameters in parallel (6 "colors" in combination with forward scatter and/or side scatter) and with an accuracy of greater than 99%. For most sorts a 4 W argon laser was used with 60 mW of power and with a 100 um nozzle. Fluorescent emissions at 488 nm excitation were collected after passage through a 530/30 nm band pass filter for FITC. Fluorescence was measured by logarithmic amplification. Cells were considered positive when fluorescence was greater than 95% of the negative control cells. A detector value of E-1 was used for forward scatter (FSC) with a mid-range amplification and, and the detector was used mid-range for side scatter (SSC) with an amplification of 1. The SSC gatings were done by means of linear amplification with division of parameters into 256 arbitrary units. Unstained cells, cells stained with an irrelevant antibody and the same fluoroprobe or with the same antibody but with no fluoroprobe were used as negative controls. In each sample, 30,000-50,000 cells were assayed. Positive cells, those with greater fluorescence than the negative controls, were evaluated further for granularity, size, and extent of fluorescence. Cells before and after sorting were maintained at 4° C. in the HDM to which 10% serum was added.

TABLE 3

Monoclonal Antibodies

| Antibodies (all prepared in mice) | Isotype/ Dilution | Target antigen (all human) | Commercial source |
|---|---|---|---|
| CD45 (31254X; 31255X) | IgG$_1$ Kappa/ 1: | Common leucocyte antigen on all hemopoietic cells | Pharmingen |
| CD 235A (32591A) | IgG$_{2b}$ Kappa/ 1: | Glycophorin A (red blood cell antigen) | |
| CD14 (APC) | IgG$_{2a}$ Kappa/ 1: | Antigen present on monocytes, dendrites, (one of the endotoxin receptors) | |
| CD34 (34374X) | IgG$_1$ Kappa/ 1: | Stem cell antigen present on diverse progenitor populations | |

TABLE 3-continued

Monoclonal Antibodies

| Antibodies (all prepared in mice) | Isotype/ Dilution | Target antigen (all human) | Commercial source |
|---|---|---|---|
| CD38 (31015X; 31014X) | $IgG_1$ Kappa/ 1: | Antigen present on B cells, thymocytes and activated T cells | |
| CAM 5.2 | $IgG_{2a}$/1:500 | CAM on ductal plate | |
| CD117 (CD11704) (MHCK04) | $IgG_{1/1}$: | c-kit: receptor for stem cell factor | Caltag |
| CD31 | $IgG_1$/1:250 | PE-CAM: CAM on endothelia | |
| ALB (A-6684) | $IgG_{2a}$/1:120 | Albumin | Sigma, St. Louis, |
| CD56 | $IgG_1$/1:250 | N-CAM: CAM on certain neurons and on ductal plate | Mo. |
| AFP (18-0003) | $IgG_1$ Kappa/1:250 | AFB | Zymed |
| CK 8/18 | $IgG_1$/ 1:1000 | Cytokeratins generic for epithelia | |
| CD146 | $IgG_1$/1:250 | M-CAM: found on endothelia | Chemicon, |
| CD133 | $IgG_1$/1: | AC 133, stem cell marker | Mylteni Biotek, |
| Ep-CAM | $IgG_1$/1:750 | A CAM on most epithelial progenitors | Neomarkers |
| CK-19 | $IgG_{2b}$/1:300 | Cytokeratin-19, keratin specific for biliary epithelia | NovCastra |

TABLE 4

Fluoroprobes

| Fluroprobes | Color | Absorbance Maximum/ Emission Maximum | 11. Source |
|---|---|---|---|
| FITC | Green | 494/525 | Sigma, St. Louis, Mo |
| Phycoerythrin (PE) | Yellow | 480/578 | Molecular Probes, |
| Alexa 488 | Green | 495/519 | Eugene, Oregon |
| 7-AAD(A-1310) used without an antibody for elimination of dead cells | Red | 488/650 | |
| Cy-5 | Far Red | 649/670 | Jackson Labs, West Row, Pennsylvania |
| AMCA | Blue | 350/450 | |

For flow cytometric analysis of cytoplasmic antigens (e.g. albumin, AFP), the cells were fixed and permeabilized with 3% paraformaldehyde prior to staining with the antisera. Cells were stained as indicated above for immunofluorescence. For analysis using 2 markers, a second antibody labeled with a distinct fluoroprobe and not overlapping in wavelength will be used. The analysis was performed using a Becton Dickenson FACscan. Cells stained only with the secondary antibody were used as negative controls. In each sample, 30,000-50,000 cells were assayed. Positive cells, those with greater fluorescence than the negative controls, were evaluated further for granularity, size, and extent of fluorescence.

Example 11

Determination of Albumin and Alpha Fetoprotein Expression in Hepatic Cell Suspension Obtained from Fetal Tissue In this experiment, the expression of albumin and alpha fetoprotein in proximal hepatic stem cells and in primitive hepatic stem cells was examined. It was initially determined that the pellet fraction is enriched for hepatoblasts (proximal hepatic stem cells) while the interface is enriched for colony forming cells (primitive hepatic stem cells).

Figure 20:
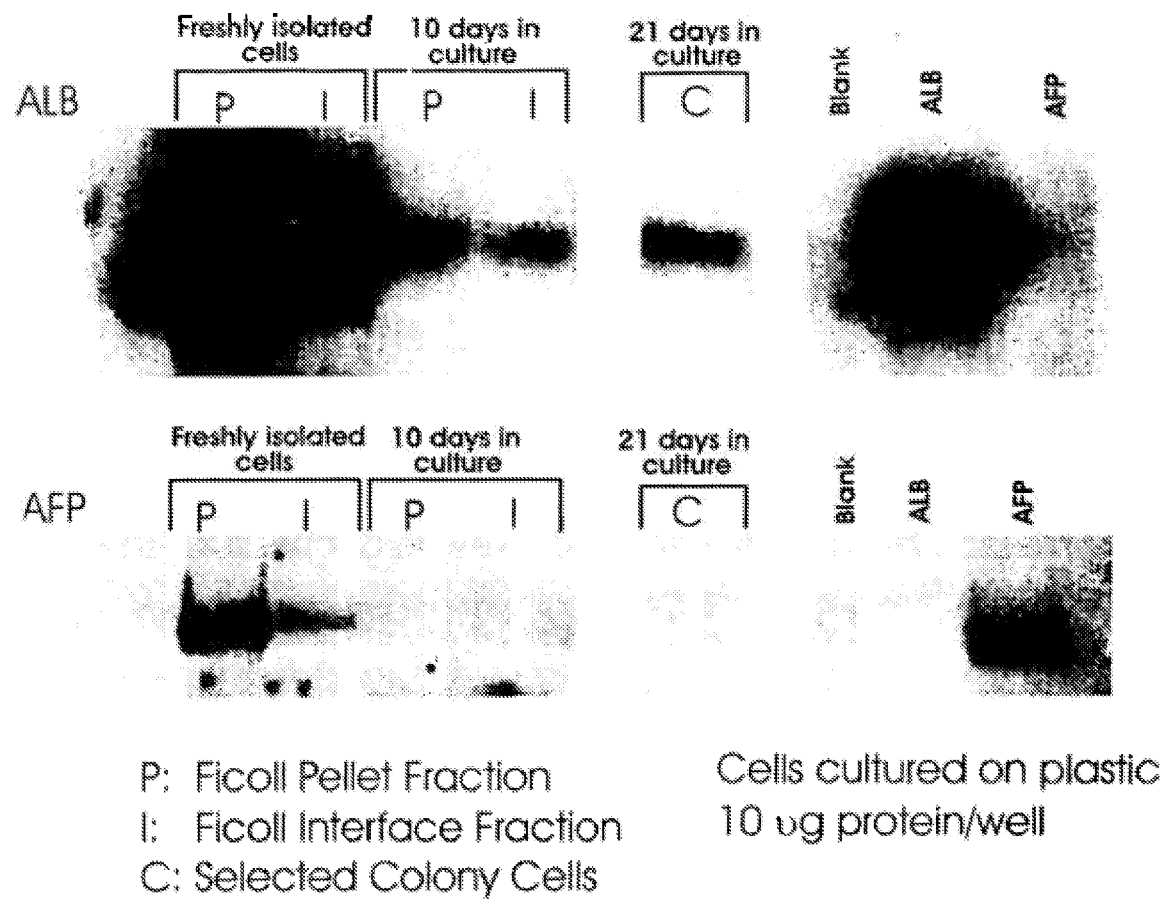
FIG. 20 depicts Western blots of albumin (ALB, upper group) and alpha fetoprotein (AFP, lower group) expression in freshly isolated fetal liver cells and during their subsequent culture on plastic substratum.

Albumin expression is comparable between interface and pellet cells, both in freshly isolated cells and after 10 days of culture. However, the expression is diminished in culture. This could be due to lower expression or proliferation of albumin negative, non parenchymal cells. Observations on the cultures indicates that both contribute to this pattern (FIG. 20).

AFP is strongly expressed in the freshly isolated pellet fraction and weakly expressed in the interface cells. This is consistent with the observation that AFP is not expressed in colony cells. After 10 days in culture AFP is not detectable in pellet or interface cells. Colony cells in culture express albumin but not AFP. This could have been due to the conditions (plastic culture) which leads to suppression of AFP expression in all cells. However, the low AFP expression in interface cells suggests that AFP is never strongly expressed in these cells (FIG. 20). Also, when colony cells are cultured in conditions that support prolonged AFP expression in pellet cells (STO co-culture) they are still negative for AFP expression. There was no crossreactivity between antibody binding to albumin or alpha fetoprotein, and no signal was observed in the empty lanes.

The results of these experiments therefore demonstrate that AFP is strongly expressed in the freshly isolated pellet fraction and only weakly expressed in the interface cells. This is consistent with the observation that AFP is not expressed in colony cells.

What is claimed is:

1. A method of isolating a human primitive hepatic stem cell, the method comprising:
   (a) providing a first single-cell suspension of cells derived from human liver tissue; then
   (b) separating hematopoietic cells and non-parenchymal cells from the first single-cell suspension, thereby yielding a second single-cell suspension; then
   (c) culturing the second single-cell suspension in serum-free media comprising insulin, transferrin and lipids to allow the single cell suspension of cells to form colonies; and then
   (d) selecting those colonies which are negative for alpha-fetoprotein (AFP) expression,
   wherein the selected colonies comprise human primitive hepatic stem cells.

2. The method of claim 1 in which the human liver tissue is fetal tissue.

3. The method of claim 1, in which the culturing is on tissue culture plastic.

4. The method of claim 1, wherein the serum-free media further comprises hydrocortisone.

5. The method of claim 1, wherein the serum-free media further comprises an antioxidant.

6. The method of claim 5, wherein the antioxidant is selenium.

7. The method of claim 1 further comprising (e) selecting from those colonies that are negative for AFP, the colonies that are further positive for Ep-CAM expression.

8. The method of claim 1 further comprising (e) selecting from those colonies of cells that are negative for AFP, the colonies which further express Ep-CAM, albumin, N-CAM, cytokeratin 19, or any combination thereof.

9. The method of claim 1 further comprising the step of removing dead cells from the single cell suspension of cells derived from human liver tissue.

10. A method of isolating human primitive hepatic stem cells, the method comprising:
    (a) providing a single cell suspension of cells derived from human fetal liver tissue; and, in any order,
    (b) selecting from the single cell suspension of cells those cells that do not express alpha-fetoprotein (AFP), but do express Ep-CAM and at least one of N-CAM, c-kit, and cytokeratin 19.

11. The method of claim 10 further comprising (c) selecting those cells from the single cell suspension expressing CD133.

12. The method of claim 10 further comprising (c) selecting those cells from the single cell suspension those cells that express albumin, cytokeratin 19, or both.

* * * * *

UNITED STATES PATENT AND TRADEMARK OFFICE
CERTIFICATE OF CORRECTION

| | |
|---|---|
| PATENT NO. | : 8,691,523 B2 |
| APPLICATION NO. | : 11/609729 |
| DATED | : April 8, 2014 |
| INVENTOR(S) | : Reid et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1847 days.

Signed and Sealed this
Eleventh Day of August, 2015

Michelle K. Lee
*Director of the United States Patent and Trademark Office*